United States Patent
Bridgham et al.

(10) Patent No.: US 9,273,354 B2
(45) Date of Patent: *Mar. 1, 2016

(54) SYSTEM AND APPARATUS FOR SEQUENTIAL PROCESSING OF ANALYTES

(71) Applicant: ILLUMINA, INC., San Diego, CA (US)

(72) Inventors: John Bridgham, Hillsborough, CA (US); Kevin Corcoran, Livermore, CA (US); George Golda, El Granada, CA (US); Michael C. Pallas, San Bruno, CA (US); Sydney Brenner, Ely (GB)

(73) Assignee: Illumina, Inc., San Diego, CA (US)

( * ) Notice: Subject to any disclaimer, the term of this patent is extended or adjusted under 35 U.S.C. 154(b) by 7 days.

This patent is subject to a terminal disclaimer.

(21) Appl. No.: 14/245,723

(22) Filed: Apr. 4, 2014

(65) Prior Publication Data

US 2014/0213464 A1    Jul. 31, 2014

Related U.S. Application Data

(60) Continuation of application No. 13/693,658, filed on Dec. 4, 2012, now Pat. No. 8,728,729, which is a continuation of application No. 11/974,239, filed on Oct. 12, 2007, now Pat. No. 8,361,713, which is a (Continued)

(51) Int. Cl.
*C12Q 1/68* (2006.01)
*C12M 1/36* (2006.01)

(Continued)

(52) U.S. Cl.
CPC ........... *C12Q 1/6874* (2013.01); *B01J 19/0046* (2013.01); *B01L 3/502715* (2013.01);

(Continued)

(58) Field of Classification Search
CPC ............... C12Q 1/6874; B01J 19/0046; B01L 3/502715
USPC .......................... 435/6.1, 91.1, 287.2; 422/502
See application file for complete search history.

(56) References Cited

U.S. PATENT DOCUMENTS 3,397,279 A    8/1968   Leonard
3,413,464 A    11/1968  Kamentsky (Continued)

FOREIGN PATENT DOCUMENTS

EP    0372524    6/1990
EP    0392546    10/1990

(Continued)

OTHER PUBLICATIONS

Abravaya et al., "Detection of point mutations with a modified ligase chain reaction (Gap-LCR)," *Nucleic Acids Research*, vol. 23, No. 4, p. 675-682 (1995).

(Continued)

*Primary Examiner* — Betty Forman
(74) *Attorney, Agent, or Firm* — Knobbe, Martens, Olson & Bear LLP

(57) ABSTRACT

An apparatus and system are provided for simultaneously analyzing a plurality of analytes anchored to microparticles. Microparticles each having a uniform population of a single kind of analyte attached are disposed as a substantially immobilized planar array inside of a flow chamber where steps of an analytical process are carried out by delivering a sequence of processing reagents to the microparticles by a fluidic system under microprocessor control. In response to such process steps, an optical signal is generated at the surface of each microparticle which is characteristic of the interaction between the analyte carried by the microparticle and the delivered processing reagent. The plurality of analytes are simultaneously analyzed by collecting and recording images of the optical signals generated by all the microparticles in the planar array. A key feature of the invention is the correlation of the sequence of optical signals generated by each microparticle in the planar array during the analytical process.

19 Claims, 10 Drawing Sheets

Related U.S. Application Data division of application No. 11/207,443, filed on Aug. 18, 2005, now Pat. No. 7,282,370, which is a division of application No. 09/908,131, filed on Jul. 17, 2001, now Pat. No. 6,969,488, which is a division of application No. 09/424,028, filed as application No. PCT/US98/11224 on May 22, 1998, now Pat. No. 6,406,848.

(51) Int. Cl.
| | |
|---|---|
| *B01J 19/00* | (2006.01) |
| *B01L 3/00* | (2006.01) |
| *G01N 21/25* | (2006.01) |
| *C40B 60/14* | (2006.01) |
| *G01N 15/14* | (2006.01) |
| *G01N 15/00* | (2006.01) |

(52) U.S. Cl.
CPC ...... *B01L3/502761* (2013.01); *G01N 15/1475* (2013.01); *G01N 15/1484* (2013.01); *G01N 21/253* (2013.01); *B01J 2219/00274* (2013.01); *B01J 2219/00317* (2013.01); *B01J 2219/00648* (2013.01); *B01J 2219/00659* (2013.01); *B01L 2200/0647* (2013.01); *B01L 2200/10* (2013.01); *B01L 2300/0877* (2013.01); *B01L 2400/0403* (2013.01); *B01L 2400/0475* (2013.01); *B01L 2400/0622* (2013.01); *B01L 2400/0644* (2013.01); *C40B 60/14* (2013.01); *G01N 15/1456* (2013.01); *G01N 2015/0015* (2013.01); *G01N 2015/149* (2013.01)

(56) References Cited

U.S. PATENT DOCUMENTS

| | | |
|---|---|---|
| 3,791,192 A | 2/1974 | Butler |
| 4,046,720 A | 9/1977 | Rembaum et al. |
| 4,123,610 A | 10/1978 | Summerton et al. |
| 4,125,828 A | 11/1978 | Resnick et al. |
| 4,180,739 A | 12/1979 | Abu-Shumays |
| 4,252,769 A | 2/1981 | Hood et al. |
| 4,354,114 A | 10/1982 | Karnukhov |
| 4,363,967 A | 12/1982 | Efkeman et al. |
| 4,558,845 A | 12/1985 | Hunkapiller |
| 4,605,630 A | 8/1986 | Kung |
| 4,661,225 A | 4/1987 | Penniman |
| 4,703,913 A | 11/1987 | Hunkapiller |
| 4,727,033 A | 2/1988 | Hijikata |
| 4,811,218 A | 3/1989 | Hunkapiller et al. |
| 4,822,746 A | 4/1989 | Walt |
| 4,883,750 A | 11/1989 | Whiteley et al. |
| 4,908,112 A | 3/1990 | Pace |
| 4,911,782 A | 3/1990 | Brown |
| 4,988,617 A | 1/1991 | Landegren et al. |
| 5,002,867 A | 3/1991 | Macevicz |
| 5,047,524 A | 9/1991 | Andrus et al. |
| 5,104,791 A | 4/1992 | Abbott et al. |
| 5,114,864 A | 5/1992 | Walt |
| 5,116,765 A | 5/1992 | Watanabe |
| 5,143,853 A | 9/1992 | Walt |
| 5,173,260 A | 12/1992 | Zander |
| 5,203,368 A | 4/1993 | Barstow et al. |
| 5,235,522 A | 8/1993 | Bacus et al. |
| 5,244,636 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,257,182 A | 10/1993 | Luck et al. |
| 5,262,127 A | 11/1993 | Wise |
| 5,298,741 A | 3/1994 | Walt et al. |
| 5,301,006 A | 4/1994 | Bruce |
| 5,308,990 A | 5/1994 | Takahashi et al. |
| 5,320,814 A | 6/1994 | Walt et al. |
| 5,326,738 A | 7/1994 | Sandoval et al. |
| 5,403,708 A | 4/1995 | Brennan et al. |
| 5,407,798 A | 4/1995 | Martinelli et al. |
| 5,415,839 A | 5/1995 | Zaun et al. |
| 5,427,946 A | 6/1995 | Kricka et al. |
| 5,429,807 A | 7/1995 | Matson et al. |
| 5,474,796 A | 12/1995 | Brennan |
| 5,478,893 A | 12/1995 | Ghosh |
| 5,479,252 A | 12/1995 | Worster et al. |
| 5,494,810 A | 2/1996 | Barany et al. |
| 5,496,697 A | 3/1996 | Parce et al. |
| 5,503,980 A | 4/1996 | Cantor |
| 5,506,141 A | 4/1996 | Weinreb et al. |
| 5,512,490 A | 4/1996 | Walt et al. |
| 5,552,278 A | 9/1996 | Brenner |
| 5,556,764 A | 9/1996 | Sizto et al. |
| 5,565,365 A | 10/1996 | Glass |
| 5,575,849 A | 11/1996 | Honda et al. |
| 5,578,832 A | 11/1996 | Trulson et al. |
| 5,587,128 A | 12/1996 | Wilding et al. |
| 5,599,668 A | 2/1997 | Stimpson et al. |
| 5,599,675 A | 2/1997 | Brenner |
| 5,604,097 A | 2/1997 | Brenner |
| 5,631,734 A | 5/1997 | Stern et al. |
| 5,633,972 A | 5/1997 | Walt et al. |
| 5,637,469 A | 6/1997 | Wilding et al. |
| 5,639,423 A | 6/1997 | Northrup |
| 5,639,603 A | 6/1997 | Dower et al. |
| 5,653,859 A | 8/1997 | Parton et al. |
| 5,667,976 A | 9/1997 | Van Ness et al. |
| 5,677,153 A | 10/1997 | Botstein et al. |
| 5,700,637 A | 12/1997 | Southern |
| 5,705,402 A | 1/1998 | Leland |
| 5,707,799 A | 1/1998 | Hansmann |
| 5,708,153 A | 1/1998 | Dower et al. |
| 5,710,000 A | 1/1998 | Sapolsky et al. |
| 5,741,647 A | 4/1998 | Tam |
| 5,750,341 A | 5/1998 | Macevicz |
| 5,763,175 A | 6/1998 | Brenner |
| 5,780,231 A | 7/1998 | Brenner |
| 5,783,401 A | 7/1998 | Toledano |
| 5,798,210 A | 8/1998 | Canard et al. |
| 5,800,992 A | 9/1998 | Fodor |
| 5,800,994 A | 9/1998 | Martinelli et al. |
| 5,804,384 A | 9/1998 | Muller et al. |
| 5,807,522 A | 9/1998 | Brown et al. |
| 5,814,524 A | 9/1998 | Walt |
| 5,827,704 A | 10/1998 | Cease et al. |
| 5,834,195 A | 11/1998 | Benkovic et al. |
| 5,846,719 A | 12/1998 | Brenner |
| 5,854,078 A | 12/1998 | Asher et al. |
| 5,854,684 A | 12/1998 | Stabile et al. |
| 5,856,093 A | 1/1999 | Brenner |
| 5,856,174 A | 1/1999 | Lipshutz |
| 5,863,722 A | 1/1999 | Brenner |
| 5,872,623 A | 2/1999 | Stabile |
| 5,876,924 A | 3/1999 | Zhang et al. |
| 5,877,280 A | 3/1999 | Wetmur |
| 5,888,723 A | 3/1999 | Sutton et al. |
| 5,889,881 A | 3/1999 | MacAulay et al. |
| 5,900,481 A | 5/1999 | Lough |
| 5,910,406 A | 6/1999 | Minter |
| 5,922,574 A | 7/1999 | Minter |
| 5,922,617 A | 7/1999 | Wang et al. |
| 5,958,703 A | 9/1999 | Dower et al. |
| 5,962,228 A | 10/1999 | Brenner |
| 5,969,119 A | 10/1999 | Macevicz |
| 5,972,619 A | 10/1999 | Drmanac et al. |
| 5,985,214 A | 11/1999 | Stylli et al. |
| 6,007,987 A | 12/1999 | Cantor et al. |
| 6,023,540 A | 2/2000 | Walt et al. |
| 6,026,174 A | 2/2000 | Palcic et al. |
| 6,027,889 A | 2/2000 | Barany et al. |
| 6,031,930 A | 2/2000 | Bacus et al. |
| 6,054,277 A | 4/2000 | Furcht et al. |
| 6,057,150 A | 5/2000 | Lee et al. |
| 6,074,609 A | 6/2000 | Gavin |
| 6,087,095 A | 7/2000 | Rosenthal et al. |
| 6,122,396 A | 9/2000 | King et al. |

(56) References Cited

U.S. PATENT DOCUMENTS

| | | | |
|---|---|---|---|
| 6,150,516 | A | 11/2000 | Brenner et al. |
| 6,151,405 | A | 11/2000 | Douglass et al. |
| 6,153,375 | A | 11/2000 | Kobylecki et al. |
| 6,172,218 | B1 | 1/2001 | Brenner |
| 6,214,560 | B1 | 4/2001 | Yguerabide et al. |
| 6,251,691 | B1 | 6/2001 | Seul |
| 6,266,459 | B1 | 7/2001 | Walt et al. |
| 6,268,148 | B1 | 7/2001 | Barany et al. |
| 6,306,597 | B1 | 10/2001 | Macevicz |
| 6,327,377 | B1 | 12/2001 | Rutenberg et al. |
| 6,327,410 | B1 | 12/2001 | Walt |
| 6,406,848 | B1 | 6/2002 | Bridgham et al. |
| 6,511,802 | B1 | 1/2003 | Albrecht et al. |
| 6,654,505 | B2 | 11/2003 | Bridgham et al. |
| 6,806,052 | B2 | 10/2004 | Bridgham et al. |
| 6,831,994 | B2 | 12/2004 | Bridgham et al. |
| 6,855,523 | B2 | 2/2005 | Zhang et al. |
| 6,969,488 | B2 | 11/2005 | Bridgham et al. |
| 7,070,927 | B2 | 7/2006 | Drmanac |
| 7,270,951 | B1 | 9/2007 | Stemple et al. |
| 7,282,370 | B2 | 10/2007 | Bridgham et al. |
| 8,361,713 | B2 | 1/2013 | Bridgham et al. |

FOREIGN PATENT DOCUMENTS

| | | |
|---|---|---|
| EP | 0514927 | 11/1992 |
| GB | 2226182 | 10/1993 |
| GB | 2236852 | 4/1997 |
| JP | 06082331 | 3/1994 |
| WO | WO 89/12695 | 12/1989 |
| WO | WO 91/06678 | 5/1991 |
| WO | WO 91/16966 | 11/1991 |
| WO | WO 93/17126 | 9/1993 |
| WO | WO 93/21340 | 10/1993 |
| WO | WO 93/22053 | 11/1993 |
| WO | WO 94/03104 | 2/1994 |
| WO | WO 94/11530 | 5/1994 |
| WO | WO 94/23064 | 10/1994 |
| WO | WO 94/27719 | 12/1994 |
| WO | WO 95/09248 | 4/1995 |
| WO | WO 95/22058 | 8/1995 |
| WO | WO 95/25737 | 9/1995 |
| WO | WO 95/35390 | 12/1995 |
| WO | WO 96/03212 | 2/1996 |
| WO | WO 96/12014 | 4/1996 |
| WO | WO 96/12039 | 4/1996 |
| WO | WO 96/15271 | 5/1996 |
| WO | WO 96/41011 | 12/1996 |
| WO | WO 97/02357 | 1/1997 |
| WO | WO 97/12030 | 4/1997 |
| WO | WO 97/14028 | 4/1997 |
| WO | WO 97/31256 | 8/1997 |
| WO | WO 97/40383 | 10/1997 |
| WO | WO 97/40385 | 10/1997 |
| WO | WO 97/43611 | 11/1997 |
| WO | WO 97/46704 | 12/1997 |
| WO | WO 98/08092 | 2/1998 |
| WO | WO 98/13523 | 4/1998 |
| WO | WO 98/31836 | 7/1998 |
| WO | WO 98/40726 | 9/1998 |
| WO | WO 98/50782 | 11/1998 |
| WO | WO 98/53093 | 11/1998 |
| WO | WO 98/53300 | 11/1998 |
| WO | WO 99/18434 | 4/1999 |
| WO | WO 99/60170 | 11/1999 |
| WO | WO 99/67641 | 12/1999 |
| WO | WO 00/13004 | 3/2000 |
| WO | WO 00/16101 | 3/2000 |
| WO | WO 00/39587 | 7/2000 |
| WO | WO 00/47996 | 8/2000 |
| WO | WO 00/48000 | 8/2000 |
| WO | WO 00/63437 | 10/2000 |
| WO | WO 00/71243 | 11/2000 |
| WO | WO 00/71992 | 11/2000 |
| WO | WO 00/71995 | 11/2000 |
| WO | WO 00/75373 | 12/2000 |

OTHER PUBLICATIONS

Abravaya et al., "Detection of Point Mutations with Ligase Chain Reaction" ASM General Meeting of the American Society for Microbiology (Las Vegas, NV) 1994.

Akane et al., "Direct Dideoxy Sequencing of Genomic DNA by Ligation-Mediated PCR," *Bio Techniques*, vol. 16, No. 2, Jan. 1994.

Baldwin et al., "Chemometric labeling of cereal tissues in multichannel fluorescence microscopy images using discriminant analysis". Anal. Chem. 1997. 69:4339-4348.

Barany, "Genetic Disease Detection and DNA Amplification Using Cloned Thermostable Ligase," *Proc. Natl. Acad. Sci. USA*, vol. 88, p. 189-193, Jan. 1991.

Barany, "The Ligase Chain Reaction in a PCR World," *PCR Methods and Applications*, vol. 1, No. 1, p. 5-16, Aug. 1991.

Brandriss, et al.,"Synthesis and Characterization of Self-Assemebled Hydrophobic Monolayer Coatings on Silica Colloids" *Langmuir* 9: 1232-1240 (1993).

Brenner, et al., "Gene Expression Analysis by Massively Parallel Signature Sequencing (MPSS) on Micorbead Arrays," *Nature Biotech*. 18:630-634 (2000).

Cantor et al., "Report on the Sequencing by Hybridization Workshop," *Genomics*, vol. 13, p. 1379-1383 (1992).

Cao, "Recent Developments in Ligase-Mediated Amplification and Detection," *Trends in Biotechnology*, vol. 22, No. 1, p. 38-44, Jan. 2004.

Carrino and Lee, "Nucleic acid amplification methods," *J. Microbiological Methods*, vol. 23, p. 3-20 (1995).

Cease, et al., "A Vector for Facile PCR Product Cloning and Modification Generating Any Desired 4-Base 5' Overhang: pRPM" *Bio Techniques* (1993) 14(2): 250-255.

Chee, et al., "Accessing Genetic Information with High-Density DNA Arrays" *Science* (1996) 274: 610-614.

Chelly et al., "Transcription of the Dystrophin Gene in Human Muscle and Non-Muscle Tissues," *Nature*, vol. 333, No. 6167, p. 858-860, Jun. 30, 1988.

Chen, J., et al., "A Microsphere-Based Assay for Multiplexed Single Nucleotide Polymorphism Analysis Using Single Base Chain Extension," *Gen. Res*. 10(4):549-557 (Apr. 2000).

Day et al., "Detection of Steroid 21-Hydroxylase Alleles Using Gene-Specific PCR and a Multiplexed Ligation Detection Reaction," *Genomics*, vol. 29, p. 152-162 (1995).

DeRisi et al., "Exploring the metabolic and genetic control of gene expression on a genomic scale.", Science, 278:680-686 (1997).

DiMilla, et al., "Maximal Migration of Human Smooth Muscle Cells on Fibronectin and Type IV Collagen Occurs at an Intermediate Attachment Strength" *J. Cell Biology* 122(3): 729-737 (1993).

Dobrynin, et al., "Plasmid Vectors pBBv for Cloning and Regeneration of DNA Fragments with Any End Nucleotide Sequence" *Reports of the USSR Academy of Sciences* (1984) 278(4): 1002-1006.

Dow, et al., "A simple microcomputer-based system for real-time analysis of cell behaviour" *J. Cell Science* 87: 171-182 (1987).

Drmanac, et al. "SBH and the Integration of Complementary Approaches in the Mapping, Sequencing, and Understanding of Complex Genomes" Technical Paper Presented at the International Conference on Bioinformatics, Supercomputing, and Complex Genome Analysis, St. Petersburg, FL (United States), Jun. 4-7, 1992.

Drmanac, et al., "Sequencing by Hybridization", Ch. 4 in *Automated DNA Sequencing and Analysis*, ed. Adams, M.D. et al., Academic Press, NY, 1994, pp. 24-36.

Drmanac, R., et al., "Prospects for a Miniaturized, Simplified and Frugal Human Genome Project," *Scientia Yugoslavica* 16(1-2):97-107 (1990).

Drmanac, et al., "Sequencing by Hybridization (SBH) with Oligonucleotide Probes as an Integral Approach for the Analysis of Complex Genomes", Inter. J. of Genome Research vol. 1 No. 1, World Scientific Publishing Co., 1992, 59-79.

(56) References Cited

OTHER PUBLICATIONS

Drmanac, et al., "Sequencing by Oligonucleotide Hybridization: A Promising Framework in Decoding of the Genome Program?", The First International Conf. of Electrophoresis.Florida State Univ., Apr. 10-13, 1990, 47-59.
Ekins, et al., "Multianalyte microspot immunoassay-Microanalytical 'compact disk' of the future", Clinical Chemistry. 37(11):1995-1967, 1991.
Fainsod et al., "The homeo domain of a murine protein binds 5' to its own homeo box," *Proc. Natl. Acad. Sci. USA*, vol. 83, p. 9532-9536, Dec. 1986.
Fodor et al., "Multiplexed biochemical assays with biological chips.", Nature, 364:555-556 (1993).
Garner et al., "High-throughput PCR." BioTechniques, 14:112-115 (1993).
Gelles, et al., "Tracking kinesin-driven movements with nanometer-scale precision" *Nature* 331: 450-453 (1988).
Gerry et al., "Universal DNA Microarray Method for Multiplex Detection of Low Abundance Point Mutations," *J. Mol. Biol.*, vol. 292, No. 2, p. 251-262 (1999).
Gilliland et al., "Analysis of cytokine mRNA and DNA: Detection and quantitation by competitive polymerase chain reaction," *Proc. Natl. Aca. Sci. USA*, vol. 87, p. 2725-2729, Apr. 1990.
Graber et al., "Advances in DNA diagnostics." Current Opinion in Biotechnology, 9:14-18 (1998).
Hiraoka et al., "The use of a charge-coupled device for quantitative optical microscopy of biological structures". Science. 1987. 238:36-41.
Horvolgyi, et al., "Monoparticulate Layers of Silanized Glass Spheres at the Water-Air Interface: Particle-Particle and Particle-Subphase Interactions" *Langmuir* 12: 997-1004 (1996).
Hsuih et al., "Novel, Ligation-Dependent PCR Assay for Detection of Hepatitis C Virus in Serum," *J. of Clin. Microbiology*, vol. 34, No. 3, p. 501-507, Mar. 1996.
Jongeneel, et al., "Comprehensive Sampling of Gene Expression in Human Cell Lines with Massively Parallel Signature Sequencing," *PNAS* 100:4702-4705 (2003).
Khrapko et al., "A Method for DNA Sequencing by Hybridization with Oligonucleotide Matrix," *DNA Sequence—J.DNA Sequencing and Mapping*, vol. 1, p. 375-388 (1991).
Khrapko et al., "Hybridization of DNA with Oligonucleotides Immobilized in Gel: Convenient Method for Recording Individual Base Changes," *Molekulyarnaya Biologiya*, vol. 25, No. 3, p. 718-730 (1991).
Kinzler and Vogelstein, "Whole genome PCR: application to the identification of sequences bound by gene regulatory proteins," *Nucleic Acids Research*, vol. 17, No. 10, p. 3645-3653 (1989).
Kramer and Lizardi, "Replicatable RNA reporters," *Nature*, vol. 339, p. 401-402, Jun. 1, 1989.
Laffler et al., "The ligase chain reaction in DNA-based diagnosis," *Ann. Biol. Clin.*, vol. 50, p. 821-826 (1993).
Lam et al., Nature, 354:82-84 (1991).
Luo et al., "Improving the fidelity of Thermus thermophilus DNA ligase," *Nucleic Acids Research*, vol. 24, No. 14, p. 3071-3078 (1996).
Lyamichev, V., et al., "Polymorphism identification and quantitative detection of genomic DNA by invasive cleavage of oligonucleotide probes," *Nat. Biotechnol.* 17:292-296 (1999).
Lysov et al., "A New Method for Determining the DNA Nucleotide Sequence by Hybridization with Oligonucleotides," Translated from Doklady Akademii Nauk SSR, vol. 303, No. 6, pp. 1508-1511, Dec. 1988.
Mag et al., "Synthesis and Selective Cleavage of an Oligodeoxynucleotide Containing a Bridged Non-Chiral Internucleotide 3'-Phosphoramidate Linkage", Tetrahedron Letters 33(48):7319-7322 (1992).
Mandecki, et al., "FokI method of *gene* synthesis" Gene (1988) 68: 101-107.
Maskos and Southern, "A study of oligonucleotide reassociation using large arrays of oligonucleotides synthesized on a glass support," *Nucleic Acids Research*, vol. 21, No. 20, p. 4663-4669 (1993).
McNamara et al., "Development of a Multiplex PCR-Ligase Detection Reaction Assay for Diagnosis of Infection by the Four Parasite Species Causing Malaria in Humans," *J. Clinical Microbiology*, p. 2403-2410, Jun. 2004.
Memorandum and Order Regarding Claim Construction, dated Dec. 15, 2010, in the matter of *Life Technologies Corp., et al.* v. *Illumina, Inc., et al.*, Case No. 11-cv-00703-JAH-POR, U.S. District Court for the Southern District of California.
Metzker et al, "Termination of DNA synthesis by novel 3'-modified-deoxyribonucleoside 5'- triphosphates.", Nucleic Acids Research, 22:4259-4267 (1994).
Michael et al., Randomly ordered addressable high-density optical sensor array. Anal. Chem. 1998. 70(7):1242-1248.
Michael, K., et al., "Fabrication of micro- and nanostructures using optical imaging fibers and their use as chemical sensors," *Proc. 3$^{rd}$ Intl Symp., Microstructures and Micorfabricated Syst.*, P.J. Hesketh et al., (eds.), Electrochem. Soc. Proc. 97(5):152-157 (Aug. 1997).
Michael, "Making Sensors out of Disarray: Optical Sensor Microarrays", Proc. SPIE, vol. 3270, 1998, 34-41.
Mirzabekov, "DNA Sequencing by Hybridization—a Megasequencing Method and a Diagnostic Tool?" *TIBTECH*, vol. 12, p. 27-32, Jan. 1994.
Mormeneo, et al., "Precise nucleotide sequence modifications with bidirectionally cleaving class-IIS excision linkers" *Gene* (1987) 61: 21-30.
Nilsson et al., "Padlock Probes: Circularizing Oligonucleotides for Localized DNA Detection," *Science*, vol. 265, p. 2085-2088, Sep. 30, 1994.
Nyren, et al., "Detection of Single-Base Changes Using a Bioluminometric Primer Extension Assay", Anal. Biochem. Jan. 15, 1997; 244 (2) 367-73., 1997, 367-73.
Nyren, et al., "Solid Phase DNA Minisequencing by an Enzymatic Luminometric Inorganic Phyrophosphate Detection Assay", Anal Biochem. Jan. 1993; 208 (1):171-5, 1993, 171-175.
Palzkill, et al., "Probing β-Lactamase Structure and Function Using Random Replacement Mutagenesis" *Proteins* (1992) 14: 29-44.
Park, et al., "Detection of Hepatitis C Virus RNA Using Ligation-Dependent Polymerase Chain Reaction in Formalin-Fixed, Paraffin-Embedded Liver Tissues," *Am. J. of Pathology*, vol. 149, No. 5, p. 1485-1491, Nov. 1996.
Pfeifer et al., "Genomic Sequencing and Methylation Analysis by Ligation Mediated PCR," *Science*, vol. 246, p. 810-813, Oct. 6, 1989.
Poustka, et al., "Construction and use of human chromosome jumping libraries from NotI-digested DNA" *Nature* (1987) 325: 353-355.
Poustka, et al., "Jumping libraries and linking libraries: the next generation of molecular tools in mammalian genetics" *TIG* (1986): 174-179.
Punwaney et al., "Human Papillomavirus may be Common within Nasopharyngeal Carcinoma of Caucasian American: Investigation of Epstein-Barr Virus and Human Papillomavirus in Easterns and Western Nasopharyngeal Carcinoma Using Ligation-Dependent Polymerase Chain Reaction," *Head & Neck*, vol. 21, No. 1, p. 21-29, Jan. 1999.
Ronaghi, M et al., "Real-time DNA sequencing using detection of pyrophosphate release", Anal. Biochem. Nov. 1, 1996; 242 (1):84-9, Nov. 1, 1996, 84-89.
Sapolsky, et al., "Mapping Genomic Library Clones Using Oligonucleotide Arrays" *Genomics* (1996) 33: 445-456.
Schmidt, et al., "Integrin-Cytoskeletal Interactions in Migrating Fibroblasts are Dynamic, Asymmetric, and Regulated" *J. Cell Biology* 123(4): 977-991 (1993).
Smith, "Ligation-mediated PCR of Restriction Fragments from Large DNA Molecules," *PCR Methods and Applications*, Aug. 1992, vol. 2, No. 1, p. 21-27.
Southern et al., "Analyzing and Comparing Nucleic Acid Sequences by Hybridization to Arrays of Oligonucleotides: Evaluation Using Experimental Models," *Genomics*, vol. 13, p. 1008-1017 (1992).
Strezoska et al., "DNA sequencing by hybridization: 100 bases read by a non-gel-based method," *Proc. Natl. Acad. Sci. USA*, vol. 88, p. 10089-10093, Nov. 1991.

(56) References Cited

OTHER PUBLICATIONS

Szybalski, et al., "Class-IIS restriction enzymes—a review" *Gene* (1991) 100: 13-26.
U.S. Department of Energy, Office of Energy Research Grant Proposal, "Sequencing of DNA by Hybridization with oligonucleotides matrix (SHOM)," Mirzabekov (Principal Investigator), Mar. 30, 1992.
Velculescu, et al., "Serial Analysis of Gene Expression" *Science* (1995) 270: 484-487.
Walt, , "Fiber-Optic Imaging Sensors", Accounts of Chemical Research, 31(5), 1998, 267-278.
Walt, D., "Fiber-optic sensors for continuous clinical monitoring," *Proc. IEEE* 80(6):903-911 (1992).
Wang et al., "Molecular Genetic and Genetic Correlations in Sodium Channelopathies: Lack of Founder Effect and Evidence for a Second Gene," *Am. J. Hum. Genet.*, vol. 52, p. 1074-1084 (1993).
Wernet, et al., "Particle displacement tracking technique and Cramer-Rao lower bound error in centroid estimates from CCD imagery" *Experiments in Fluids*, 15: 295-307 (1993).
Wiedmann et al. "Detection of Listeria monocytogenes with a Nonisotopic Polymerase Chain Reaction-Coupled Ligase Chain Reaction Assay," *Applied and Environmental Microbiology*, vol. 59, No. 8, p. 2743-2745, Aug. 1993.
Wiedmann et al., "Discrimination of Other Listeria Species by Ligase Chain Reaction," *Applied and Environmental Microbiology*, vol. 58, No. 11, p. 3443-3447, Nov. 1992.
Wiedmann et al., "Ligase Chain Reaction (LCR)—Overview and Applications," *PCR Methods and Applications*, vol. 3, No. 4, p. S51-S64, Feb. 1994.
Wilson et al., "Frequency of oncogenic point mutations in human tissues determined by combined PCR and LCR techniques," *Proceedings of the American Association for Cancer Research*, vol. 34, p. 262, Mar. 1993.
Wilson, et al., "Single particle tracking of cell-surface HLA-DR molecules using R-phycoerythrin labeled monoclonal antibodies and fluorescence digital imaging" *J. Cell Science* 109: 2101-2109 (1996).
Wu and Wallace, "The Ligation Amplification Reaction (LAR)—Amplification of Specific DNA Sequences Using Sequential Rounds of Template-Dependent Ligation," *Genomics*, vol. 4, p. 560-569 (1989).
Wodicka et al., "Genome-wide expression monitoring in *Saccharomyces cerevisiae*.", Nature Biotechnology, 15:1359-1367 (1997).
Yarkin et al., "Detection of HPV DNA in Cervical Specimens Collected in Cytologic Solution by Ligation-Dependent PCR," *J. of Clin. Cytology and Cytopathology*, May—vol. 47, No. 3, p. 450-456, Jun. 2003.
Life Technologies' Answer and Defenses to Defendants', Illumina and Solexa's, Counterclaims and Counter-counterclaims, dated Nov. 5, 2009, in the matter of *Life Technologies Corp.* v. *Illumina, Inc.*, 09-706 RK, U.S. District Court for the District of Delaware.
Life Technologies' Responses to Illumina and Solexa's First Set of Interrogatories, dated Dec. 21, 2009, in the matter of *Life Technologies Corp.* v. *Illumina, Inc.*, 09-706 RK, U.S. District Court for the District of Delaware, Oct. 16, 2012.
Life Technologies' Amended Answer and Defenses to Defendants', Illumina and Solexa's, Counterclaims and Counter-counterclaims, dated Jan. 29, 2010, in the matter of *Life Technologies Corp.* v. *Illumina, Inc.*, 09-706 RK, U.S. District Court for the District of Delaware, May 27, 2010.
Illumina and Solexa's Answer to the Amended Counter-counterclaims of Life Technologies, dated Feb. 12, 2010, in the matter of *Life Technologies Corp.* v. *Illumina, Inc.*, 09-706 RK, U.S. District Court for the District of Delaware.
Life Technologies' First Supplemental Response to Illumina and Solexa's Interrogatories Nos. 2, 3, 8, and 10, dated Feb. 26, 2010, in the matter of *Life Technologies Corp.* v. *Illumina, Inc.*, 09-706 RK, U.S. District Court for the District of Delaware, Oct. 16, 2012.
Exhibit A (Claim Charts Aligning References to the Claims of U.S. Pat. No. 6,554,505) to Life Technologies' Revised First Supplemental Response to Illumina and Solexa's Interrogatories Nos. 2, 3, 8, and 10, dated Feb. 26, 2010, in the matter of *Life Technologies Corp.* v. *Illumina, Inc.*, 09-706 RK, U.S. District Court for the District of Delaware.
Exhibit B (Claim Charts Aligning References to the Claims of U.S. Pat. No. 6,831,994) to Life Technologies' Revised First Supplemental Response to Illumina and Solexa's Interrogatories Nos. 2, 3, 8, and 10, dated Feb. 26, 2010, in the matter of *Life Technologies Corp.* v. *Illumina, Inc.*, 09-706 RK, U.S. District Court for the District of Delaware.
Life Technologies' Revised First Supplemental Response to Illumina and Solexa's Interrogatories Nos. 2, 3, 8, and 10, dated Feb. 26, 2010, in the matter of *Life Technologies Corp.* v. *Illumina, Inc.*, 09-706 RK, U.S. District Court for the District of Delaware.
Exhibit A (Claim Charts Aligning References to the Claims of U.S. Pat. No. 6,554,505) to Life Technologies' First Supplemental Response to Illumina and Solexa's Interrogatories Nos. 2, 3, 8, and 10, dated Feb. 26, 2010, in the matter of *Life Technologies Corp.* v. *Illumina, Inc.*, 09-706 RK, U.S. District Court for the District of Delaware.
Exhibit B (Claim Charts Aligning References to the Claims of U.S. Pat. No. 6,831,994) to Life Technologies' First Supplemental Response to Illumina and Solexa's Interrogatories Nos. 2, 3, 8, and 10, dated Feb. 26, 2010, in the matter of *Life Technologies Corp.* v. *Illumina, Inc.*, 09-706 RK, U.S. District Court for the District of Delaware.
Joint Claim Construction Chart and Statement, in the matter of *Life Technologies Corp.* v. *Illumina, Inc.*, 09-706 RK, U.S. District Court for the District of Delaware, Dec. 15, 2010.
Exhibit A (Stipulated Constructions for Identified Terms in the Patents-In-Suit) to Amended Joint Claim Construction Chart and Statement, in the matter of *Life Technologies Corp.* v. *Illumina, Inc.*, 09-706 RK, U.S. District Court for the District of Delaware Dec. 15, 2010.
Exhibit B (Proposed Constructions for Identified Terms) to Amended Joint Claim Construction Chart and Statement, in the matter of *Life Technologies Corp.* v. *Illumina, Inc.*, 09-706 RK, U.S. District Court for the District of Delaware Dec. 15, 2010.
Amended Joint Claim Construction Chart and Statement, in the matter of *Life Technologies Corp.* v. *Illumina, Inc.*, 09-706 RL, U.S. District Court for the District of Delaware.
Amended Exhibit A (Stipulated Constructions for Identified Terms in the Patents-In-Suit) to Amended Joint Claim Construction Chart and Statement, in the matter of *Life Technologies Corp.* v. *Illumina, Inc.*, 09-706 RK, U.S. District Court for the District of Delaware May 7, 2010.
Amended Exhibit B (Proposed Constructions for Identified Terms) to Amended Joint Claim Construction Chart and Statement, in the matter of *Life Technologies Corp.* v. *Illumina, Inc.*, 09-706 RK, U.S. District Court for the District of Delaware dated May 7, 2010.
Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Exhibit A (Oxford Dictionary of Biochemistry and Microbiology) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Exhibit B (Glossary of Chemical Terms) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.
Exhibit C (McGraw-Hill Dictionary of Chemistry) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.

(56) References Cited

OTHER PUBLICATIONS

Exhibit D (Grant & Hackh's Chemical Dictionary) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.

Exhibit E (Dictionary.com) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.

Exhibit F (McGraw-Hill Dictionary of Scientific and Technical Terms) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.

Exhibit G (Webster's Third New International Dictionary) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.

Exhibit H (Roget's 21st Century Thesaurus) to Declaration of Cullen N. Pendleton in Support of Illumina and Solexa's Opening Claim Construction Brief, dated May 27, 2010, in the matter of Life *Technologies Corp.* v. *Illumina, Inc.*, 09-706 RK, U.S. District Court for the District of Delaware.

Exhibit I (U.S. Pat. No. 4,125,828) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.

Exhibit J (Academic Press Dictionary of Science and Technology) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.

Exhibit K (Dictionary.com) to Declaration of Cullen N. Pendleton in Support of Illumina and Solexa's Opening Claim Construction Brief, dated May 27, 2010, in the matter of *Life Technologies Corp.* v. *Illumina, Inc.*, 09-706 RK, U.S. District Court for the District of Delaware.

Life Technologies' Opening Claim Construction Brief, dated May 27, 2010, in the matter of *Life Technologies Corp.* v. *Illumina, Inc.*, 09-706 RK, U.S. District Court for the District of Delaware, Jun. 7, 2010.

Exhibit A (Exemplary Claim Terms) to Life Technologies' Opening Claim Construction Brief, dated May 27, 2010, in the matter of *Life Technologies Corp.* v. *Illumina, Inc.*, 09-706 RK, U.S. District Court for the District of Delaware.

Exhibit B (Amendment and Response to Office Action in Inter Partes Reexamination, filed May 21, 2010 in Reexamination Control No. 95/001,292) to Life Technologies' Opening Claim Construction Brief, dated May 27, 2010, in the matter of *Life Technologies Corp.* v. *Illumina, Inc.*, 09-706 RK, U.S. District Court for the District of Delaware.

Exhibit C (Amendment and Reply to Office Action in Inter Partes Reexamination, filed May 21, 2010 in Reexamination Control No. 95/000,527) to Life Technologies' Opening Claim Construction Brief, dated May 27, 2010, in the matter of *Life Technologies Corp.* v. *Illumina, Inc.*, 09-706 RK, U.S. District Court for the District of Delaware.

Exhibit D (American Heritage Dictionary of the English Language) to Life Technologies' Opening Claim Construction Brief, dated May 27, 2010, in the matter of *Life Technologies Corp.* v. *Illumina, Inc.*, 09-706 RK, U.S. District Court for the District of Delaware.

Exhibit E (The Merriam-Webster Dictionary) to Life Technologies' Opening Claim Construction Brief, dated May 27, 2010, in the matter of *Life Technologies Corp.* v. *Illumina, Inc.*, 09-706 RK, U.S. District Court for the District of Delaware.

Exhibit F (Concise Dictionary of Biomedicine and Molecular Biology) to Life Technologies' Opening Claim Construction Brief, dated May 27, 2010, in the matter of *Life Technologies Corp.* v. *Illumina, Inc.*, 09-706 RK, U.S. District Court for the District of Delaware.

Exhibit G (Human Molecular Genetics 2) to Life Technologies' Opening Claim Construction Brief, dated May 27, 2010, in the matter of *Life Technologies Corp.* v. *Illumina, Inc.*, 09-706 RK, U.S. District Court for the District of Delaware.

Exhibit H (Amendment filed Feb. 2, 2006 in U.S. Appl. No. 10/706,118) to Life Technologies' Opening Claim Construction Brief, dated May 27, 2010, in the matter of *Life Technologies Corp.* v. *Illumina, Inc.*, 09-706 RK, U.S. District Court for the District of Delaware.

Exhibit I (Classification Definitions) to Life Technologies' Opening Claim Construction Brief, dated May 27, 2010, in the matter of *Life Technologies Corp.* v. *Illumina, Inc.*, 09-706 RK, U.S. District Court for the District of Delaware.

Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.

Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.

Exhibit A (Chetverina and Chetverin) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.

Exhibit B (Molecular Biology of the Cell) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.

Exhibit C (Sakai et al.) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.

Exhibit D (WO 91/07486) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.

Exhibit E (Applied Biosytsems Solid 4 System Sets Software) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.

Exhibit F (Applied Biosytsems Solid EZ Bead System) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.

Exhibit G (Amendment and Response to Office Action in Inter Partes Reexamination, filed May 21, 2010 in Reexamination Control No. 95/001,292) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.

Exhibit H (Comments by Third Party Requester to Patent Owner's Amendment and Reply to Office Action in Inter Partes Reexamination, filed Jun. 21, 2010 in Reexamination Control No. 95/000,527) to Declaration of Cullen N. Pendleton in Support of Illumina and Solexa's Responsive Claim Construction Brief, dated Jun. 25, 2010, in the matter of *Life Technologies Corp.* v. *Illumina, Inc.*, 09-706 RK, U.S. District Court for the District of Delaware.

Life Technologies' Responsive Claim Construction Brief, dated Jun. 25, 2010, in the matter of *Life Technologies Corp.* v. *Illumina, Inc.*, 09-706 RK, U.S. District Court for the District of Delaware, Oct. 16, 2012.

Exhibit A (Academic Press Dictionary of Science and Technology) to Life Technologies' Responsive Claim Construction Brief, dated Jun.

(56) References Cited

OTHER PUBLICATIONS 25, 2010, in the matter of *Life Technologies Corp.* v. *Illumina, Inc.*, 09-706 RK, U.S. District Court for the District of Delaware.
Exhibit B (American Heritage Dictionary of the English Language) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit C (*Arbitron* v. *International Demographics, Inc.*) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit D (Webster's Third New International Dictionary) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit E (Roget's 21st Century Thesaurus) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit F (Substitute Petition to the Director under 37 C.F.R. § 1.78, filed Jun. 17, 2010 in Reexamination Control No. 95/001,292) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit I (Dictionary.com) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit G (Oxford Dictionary of Biochemistry and Molecular Biology) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit H (Webster's Third New International Dictionary) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit J (Academic Press Dictionary of Science and Technology) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit K (The American Heritage Dictionary of the English Language) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit L (The Merriam-Webster Dictionary) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Exhibit M (*Vizio, Inc.* v. *International Trade Commission*) to Life Technologies' Responsive Claim Construction Brief, dated Jun. 25, 2010, in the matter of *Life Technologies Corp.* v. *Illumina, Inc.*, 09-706 RK, U.S. District Court for the District of Delaware.
Joint Appendix for Claim Construction Briefs, in the matter of *Life Technologies Corp.* v. *Illumine, Inc.*, 09-706 RK, U.S. District Court for the District of Delaware Dec. 15, 2010.
Cited Documents in Joint Appendix for Claim Construction Briefs, in the matter of *Life Technologies Corp.* v. *Illumine, Inc.*, 09-706 RK, U.S. District Court for the District of Delaware Dec. 15, 2010.
Illumina's Slides for Markman Hearing, in the matter of *Life Technologies Corp.* v. *Illumine, Inc.*, 09-706 RK, U.S. District Court for the District of Delaware, May 25, 2010.
Life Technologies' Slides for Markman Hearing, in the matter of *Life Technologies Corp.* v. *Illumina, Inc.* 09-706 RK U.S. District Court for the District of Delaware Feb. 13, 2008.
Complaint, dated May 31, 2007, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Answer of Defendants Illumina, Inc. and Solexa Inc. and Counterclaims of Defendants Solexa Inc., dated Aug. 13, 2007, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Applied Biosystems' Reply to Solexa's Counterclaims, dated Sep. 7, 2007, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Applied Biosystems' First Amended Reply to Solexa's Counterclaims, dated Sep. 20, 2007, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Preliminary Infringement Contentions of Counterclaim Plaintiff Solexa, Inc., dated Oct. 4, 2007, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Exhibit A—U.S. Pat. No. 5,750,341 Infringement Claim Chart in *Applera Corp.,—Applied Biosystems Group* v. *Illumina, Inc., Solexa Inc.*, and *Stephen C. Macevicz*, 07-02845 WHA, U.S. District Court for the Northern District of California Oct. 4, 2007.
Exhibit B—U.S. Pat. No. 5,969,119 Infringement Claim Chart, dated Oct. 4, 2007, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Exhibit C—U.S. Pat. No. 6,306, 597 Infringement Claim Chart, dated Oct. 4, 2007, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Exhibit D—"The Future Is Solid," Dec. 5, 2006, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Exhibit E—Solid System Data—2 Base Encoding, Oct. 16, 2006, dated Oct. 4, 2007, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Exhibit F—2006 UBS East Coast Life Sciences Bus Tour, Aug. 15, 2006, dated Oct. 4, 2007, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Applied Biosystems' Second Amended Reply to Solexa's Counterclaims, dated Nov. 7, 2007, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
First Amended Complaint, dated Nov. 8, 2007, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Exhibits A-E to Applera Corp.—Applied Biosystems Group's Preliminary Invalidity Contentions, dated Nov. 19, 2007, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Answer to Amended Complaint, Counterclaim against Applera Corp.—Applied Biosystems Group, dated Nov. 27, 2007, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Patent Local Rule 4-1(a) Disclosure of Counterclaim Plaintiff Solexa, Inc., dated Nov. 27, 2007, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Patent Local Rule 4-2 Claim Construction Disclosures of Counterclaim Plaintiff Solexa, Inc., dated Dec. 7, 2007, in the matter of

(56) References Cited

OTHER PUBLICATIONS

*Applera Corp.,—Applied Biosystems Group* v. *Illumina, Inc., Solexa Inc.,* and *Stephen C. Macevicz,* 07-02845 WHA, U.S. District Court for the Northern District of California.
Applied Biosystems' Reply to Solexa's Counterclaims to First Amended Complaint, dated Dec. 20, 2007, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Opening Claim Construction Brief of Counterclaim Plaintiff Solexa, Inc., dated Jan. 4, 2008, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Declaration of John R. Labbe in Support of Opening Claim Construction Brief of Counterclaim Plaintiff Solexa, Inc., dated Jan. 4, 2008, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Exhibits A-D to Declaration of John R. Labbe (Ex. A-Ab's Proposed Terms and Claim Elements for Construction; Ex. B-Ab's Preliminary Claim Constructions and Extrinsic Evidence; Ex. C-Amendment dated Dec. 16, 1996; and Ex. D-Applied Biosystems Group's Preliminary Invalidity Contentions), dated Jan. 4, 2008, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Applera Corp.—Applied Biosystems Group's Responsive Claim Construction Brief, dated Jan. 21, 2008, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Declaration of Eric C. Pai in Support of Applera Corp.—Applied Biosystems Group's Opposition to Solexa's Motion for Partial Summary Judgment of Infringement, dated Jul. 31, 2009, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Exhibit C of Pai Declaration in Support of Claim Construction—Office Action dated Apr. 16, 1996.
Exhibit D of Pai Declaration in Support of Claim Construction—Amendment dated Oct. 16, 1996.
Exhibit E of Pai Declaration in Support of Claim Construction—Notice of Allowability dated Apr. 16, 1996.
Exhibit F of Pai Declaration in Support of Claim Construction—Media Viewer: Sequencing-By-Synthesis Demo.: Illumina, Inc. dated Apr. 16, 1996.
Exhibit G of Pai Declaration in Support of Claim Construction—Article, "A High-Resolution, Flourescence-Based, Semiautomated Method for DNA Fingerprinting" dated Apr. 16, 1996.
Exhibit H of Pai Declaration in Support of Claim Construction—Article, "DNA Fingerprinting by Sampled Sequencing" dated Apr. 16, 1996.
Exhibit I of Pai Declaration in Support of Claim Construction—Amendment , dated May 12, 2000.
Reply Claim Construction Brief of Counterclaim Plaintiff Solexa, Inc., dated Jan. 25, 2008, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Declaration of John R. Labbe in Support of Reply Claim Construction Brief of Counterclaim Plaintiff Solexa, Inc., dated Jan. 25, 2008, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Exhibit 1—Celeste Yanisch-Perron et al., "Improved M13 Phage Cloning Vectors and Host Strains: Nucleotide Sequences of the M13mp18 and pUC19 Vectors," published in 1985 in vol. 33 of the journal Gene, at pp. 103 through 119. As filed in *Applera Corp.,—Applied Biosystems Group* v. *Illumina, Inc., Solexa Inc.,* and *Stephen C. Macevicz,* 07-02845 WHA, U.S. District Court for the Northern District of California.
Transcript of Proceedings, Markman hearing held on Feb. 13, 2008.
Claim Construction Order, dated Feb. 21, 2008 in *Applera Corp.,—Applied Biosystems Group* v. *Illumina, Inc., Solexa Inc.,* and *Stephen C. Macevicz,* 07-02845 WHA, U.S. District Court for the Northern District of California.
Final Infringement Contentions of Counterclaim Plaintiff Solexa, Inc., dated Mar. 24, 2008, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Exhibit A—U.S. Pat. No. 5,750,341 Infringement Claim Chart, dated Oct. 4, 2007, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Exhibit B—U.S. Pat. No. 5,969,119 Infringement Claim Chart, in the matter of *Applera Corp.,—Applied Biosystems Group* v. *Illumina, Inc., Solexa Inc.,* and *Stephen C. Macevicz,* 07-02845 WHA, U.S. District Court for the Northern District of California Oct. 4, 2007.
Exhibit C—U.S. Pat. No. 6,306, 597 Infringement Claim Chart, in the matter of *Applera Corp.,—Applied Biosystems Group* v. *Illumina, Inc., Solexa Inc.,* and *Stephen C. Macevicz,* 07-02845 WHA, U.S. District Court for the Northern District of California Feb. 21, 2008.
Exhibit E—Solid System Data—Base Encoding, Oct. 16, 2006, dated Oct. 4, 2007, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Applera Corp.—Applied Biosystems Group's Final Invalidity Contentions, dated Apr. 11, 2008, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Solexa, Inc.'s Responses and Objections to Applera Corp.—Applied Biosystems Group's First Set of Interrogatories to Solexa, Inc. (Nos. 1-3), dated Apr. 14, 2008, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Solexa, Inc.'s Responses and Objections to Applera Corp.—Applied Biosystems Group's Second Set of Interrogatories to Solexa, Inc. (Nos. 4-5), dated Apr. 28, 2008, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Solexa, Inc.'s Responses and Objections to Applera Corp.—Applied Biosystems Group's Third Set of Interrogatories to Solexa, Inc. (Nos. 6-25), dated May 30, 2008, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Expert Report of Michael L. Metzker, Ph.D., dated May 30, 2008, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Expert Report of D. Ross Sibson, Ph.D., dated May 30, 2008, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Expert Rebuttal Statement of John E. Quackenbush, Ph.D., dated Jun. 13, 2008, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.
Expert Rebuttal Statement of Keith C. Backman, Ph.D., dated Jun. 13, 2008, in the matter of *Applera Corp.,—Applied Biosystems Group* v. *Illumina, Inc., Solexa Inc.,* and *Stephen C. Macevicz,* 07-02845 WHA, U.S. District Court for the Northern District of California.

(56) References Cited

OTHER PUBLICATIONS

Solexa's Motion for Partial Summary Judgment of Infringement, dated Jul. 17, 2008, in the matter of *Applera Corp.,—Applied Biosystems Group* v. *Illumina, Inc., Solexa Inc.*, and *Stephen C. Macevicz*, 0702845 WHA, U.S. District Court for the Northern District of California.

Declaration of Cullen N. Pendleton in Support of Solexa's Motion for Partial Summary Judgment of Infringement, dated Jul. 17, 2008, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.

Exhibit 1 to Pendleton Declaration (U.S. Pat. No. 5,750,341), Principles of Di-Base Sequencing and the Advantages of Color Space Analysis in the SOLiD System Aug. 7, 2008.

Exhibit 2 to Pendleton Declaration (Amendment to U.S. Appl. No. 08/872,446 (U.S. Pat. No. 5,969,119)), Principles of Di-Base Sequencing and the Advantages of Color Space Analysis in the SOLiD System Aug. 7, 2008.

Exhibit 3 to Pendleton Declaration (AB production bearing Bates Nos. AB00137634-48), Principles of Di-Base Sequencing and the Advantages of Color Space Analysis in the SOLiD System Aug. 7, 2008.

Exhibit 4 to Pendleton Declaration (selected pages from deposition of Gina Costa taken May 20, 2008), Principles of Di-Base Sequencing and the Advantages of Color Space Analysis in the SOLiD System.

Exhibit 5 to Pendleton Declaration (AB production bearing Bates Nos. AB00121768 and AB00121773-774), Principles of Di-Base Sequencing and the Advantages of Color Space Analysis in the SOLiD System Aug. 7, 2008.

Exhibit 6 to Pendleton Declaration (AB production bearing Bates Nos. AB00134506 and AB00134513-14), Principles of Di-Base Sequencing and the Advantages of Color Space Analysis in the SOLiD System Aug. 7, 2008.

Exhibit 7 to Pendleton Declaration (AB production bearing Bates Nos. AB00136589), Principles of Di-Base Sequencing and the Advantages of Color Space Analysis in the SOLiD System Jul. 17, 2008.

Exhibit 8 to Pendleton Declaration (pages from SOLiD System User Guide (Bates Nos. AB00000683, -701, -727, -803, -875, and -905), Principles of Di-Base Sequencing and the Advantages of Color Space Analysis in the SOLiD System Jul. 17, 2008.

Exhibit 9 to Pendleton Declaration (pages from SOLiD System 2.0 Site Preparation Guide (Bates Nos. AB00007839 and -77), Principles of Di-Base Sequencing and the Advantages of Color Space Analysis in the SOLiD System Jul. 17, 2008.

Exhibit 10 to Pendleton Declaration (pages from SOLiD System 2.0 User Guide (Bates Nos. AB00008191 and AB00008317-18), Principles of Di-Base Sequencing and the Advantages of Color Space Analysis in the Solid System Jul. 17, 2008.

Exhibit 11 to Pendleton Declaration (pages from the Rebuttal Expert Report of Michael L. Metzker), Principles of Di-Base Sequencing and the Advantages of Color Space Analysis in the SOLiD System dated Jul. 17, 2008.

Exhibit 12 to Pendleton Declaration (pages from deposition of Michael Metzker taken Jun. 27, 2008), Principles of Di-Base Sequencing and the Advantages of Color Space Analysis in the SOLiD System Jul. 17, 2008.

Exhibit 13 to Pendleton Declaration (shockwave animation file—operation of the one-base encoding SOLiD System (Bates No. ILL050324)), Principles of Di-Base Sequencing and the Advantages of Color Space Analysis in the SOLiD System Jul. 17, 2008.

Exhibit 14 to Pendleton Declaration (AB production bearing Bates Nos. AB00296964 and -78), Principles of Di-Base Sequencing and the Advantages of Color Space Analysis in the SOLiD System Aug. 7, 2008 Jul. 17, 2008.

Exhibit 15 to Pendleton Declaration (AB production bearing Bates Nos. AB00245396-403), Principles of Di-Base Sequencing and the Advantages of Color Space Analysis in the SOLiD System Jul. 17, 2008.

Applera Corp.—Applied Biosystems Group's Notice of Motion and Motion for Summary Judgment of Noninfringment, dated Jul. 17, 2008, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.

Appendix A, Figure 1 to AB's Motion for Summary Judgment of Noninfringement, in the matter of *Applera Corp.,—Applied Biosystems Group* v. *Illumina, Inc., Solexa Inc.*, and *Stephen C. Macevicz*, 07-02845 WHA, U.S. District Court for the Northern District of California Jul. 17, 2008.

Appendix A, Figure 2 to AB's Motion for Summary Judgment of Noninfringment, in the matter of *Applera Corp.,—Applied Biosystems Group* v. *Illumina, Inc., Solexa Inc.*, and *Stephen C. Macevicz*, 07-02845 WHA, U.S. District Court for the Northern District of California Jul. 17, 2008.

Appendix A, Figure 3 to AB's Motion for Summary Judgment of Noninfringement, in the matter of *Applera Corp.,—Applied Biosystems Group* v. *Illumina, Inc., Solexa Inc.*, and *Stephen C. Macevicz*, 07-02845 WHA, U.S. District Court for the Northern District of California Jul. 17, 2008.

Declaration of Gina Costa, Ph.D., in Support of Applera Corp.—Applied Biosystems Group's Motion for Summary Judgment of Noninfringement, dated Jul. 17, 2008, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.

Figure 1 to Costa Declaration, in the matter of *Applera Corp.,—Applied Biosystems Group* v. *Illumina, Inc., Solexa Inc.*, and *Stephen C. Macevicz*, 07-02845 WHA, U.S. District Court for the Northern District of California Jul. 17, 2008.

Figure 2 to Costa Declaration, in the matter of *Applera Corp.,—Applied Biosystems Group* v. *Illumina, Inc., Solexa Inc.*, and *Stephen C. Macevicz*, 07-02845 WHA, U.S. District Court for the Northern District of California Jul. 17, 2008.

Declaration of Lee Jones in Support of Applera Corp.—Applied Biosystems Group's Motion for Summary Judgment of Noninfringement, dated Jul. 17, 2008, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.

Exhibit A to Jones Declaration (Specification Sheet—Applied Biosystems SOLiD System 2.0), in the matter of *Applera Corp.,—Applied Biosystems Group* v. *Illumina, Inc., Solexa Inc.*, and *Stephen C. Macevicz*, 07-02845 WHA, U.S. District Court for the Northern District of California Jul. 17, 2008.

Exhibit B to Jones Declaration (Principles of Di-Base Sequencing and the Advantages of Color Space Analysis in the SOLiD System), in the matter of *Applera Corp.,—Applied Biosystems Group* v. *Illumina, Inc., Solexa Inc.*, and *Stephen C. Macevicz*, 07-02845 WHA, U.S. District Court for the Northern District of California Jul. 17, 2008.

Declaration of Eugene Myers, Ph.D., in Support of Applera Corp.—Applied Biosystems Group's Motion for Summary Judgment of Noninfringement, dated Jul. 17, 2008, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.

Attachment 1 to Myers Declaration (Expert Report of Eugene Myers, Ph.D.), in the matter of *Applera Corp.,—Applied Biosystems Group* v. *Illumina, Inc., Solexa Inc.*, and *Stephen C. Macevicz*, 07-02845 WHA, U.S. District Court for the Northern District of California Jul. 17, 2008.

Declaration of Michael L. Metzker, Ph.D. In Support of Applera Corp.—Applied Biosystems Group's Opposition to Solexa's Motion for Partial Summary Judgment of Infringement, dated Jul. 31, 2008, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.

Exhibit 1 to Metzker Declaration (Rebuttal Expert Report of Michael L. Metzker, Ph.D.), in the matter of *Applera Corp.,—Applied Biosystems Group* v. *Illumina, Inc., Solexa Inc.*, and *Stephen C. Macevicz*, 07-02845 WHA, U.S. District Court for the Northern District of California Jul. 17, 2008.

(56) References Cited

OTHER PUBLICATIONS

Exhibit 2 to Metzker Declaration (CV of Michael L. Metzker), in the matter of *Applera Corp.,—Applied Biosystems Group v. Illumina, Inc., Solexa Inc.*, and *Stephen C. Macevicz*, 07-02845 WHA, U.S. District Court for the Northern District of California Jul. 17, 2008.
Declaration of Steven E. Comer in Support of Applera Corp.—Applied Biosystems Group's Motion for Summary Judgment of Noninfringement, dated Jul. 17, 2008, in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit A to Comer Declaration (U.S. Pat. No. 5,750,341), in the matter of *Applera Corp.,—Applied Biosystems Group v. Illumina, Inc., Solexa Inc.*, and *Stephen C. Macevicz*, 07-02845 WHA, U.S. District Court for the Northern District of California Feb. 21, 2008.
Exhibit B to Comer Declaration (U.S. Pat. No. 5,969,119), in the matter of *Applera Corp.,—Applied Biosystems Group v. Illumina, Inc., Solexa Inc.*, and *Stephen C. Macevicz*, 07-02845 WHA, U.S. District Court for the Northern District of California Feb. 21, 2008.
Exhibit C to Comer Declaration (U.S. Pat. No. 6,306,597), in the matter of *Applera Corp.,—Applied Biosystems Group v. Illumina, Inc., Solexa Inc.*, and *Stephen C. Macevicz*, 07-02845 WHA, U.S. District Court for the Northern District of California Jan. 18, 2008.
Exhibit D to Comer Declaration (Office Action from Patent Examiner mailed Apr. 16, 1996 from file history of U.S. Appl. No. 08/424,663), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit E to Comer Declaration (Amendment dated Oct. 16, 1996 from file history of U.S. Appl. No. 08/424,663), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit F to Comer Declaration (Office Action from Patent Examiner mailed Dec. 12, 1997 from file history of U.S. Appl. No. 08/872,446), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit G to Comer Declaration (Amendment dated May 12, 1998 from file history of U.S. Appl. No. 08/872,446), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit H to Comer Declaration (Solexa's Patent Local Rule 4-2(a) Disclosures dated Dec. 7, 2007), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit I to Comer Declaration (Expert Statement of Keith C. Backman re: Infringement dated May 30, 2008), in the matter of *Applera Corp.,—Applied Biosystems Group v. Illumina, Inc., Solexa Inc.*, and *Stephen C. Macevicz*, 07-02845 WHA, U.S. District Court for the Northern District of California dated May 27, 2010.
Exhibit J to Comer Declaration (Expert Rebuttal Statement of John E. Quackenbush dated Jun. 13, 2008), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit K to Comer Declaration (Excerpts from the deposition of Keith C. Backman taken Jun. 27, 2008), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit L to Comer Declaration (Excerpts from the deposition of John Quackenbush taken Jul. 1, 2008), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit M to Comer Declaration (Excerpts from the Rule 30(b)(6) deposition of Gina Costa taken May 20, 2008), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit N to Comer Declaration (U.S. Appl. No. 08/424,663), in the matter of *Applera Corp.,—Applied Biosystems Group v. Illumina, Inc., Solexa Inc.*, and *Stephen C. Macevicz*, 07-02845 WHA, U.S. District Court for the Northern District of California, Oct. 4, 2007.
Exhibit O to Comer Declaration (Solexa's Final Infringement Contentions dated Mar. 24, 2008).
Exhibit P to Comer Declaration (CD of the source code for the SOLiD System), in the matter of *Applera Corp.,—Applied Biosystems Group v. Illumina, Inc., Solexa Inc.*, and *Stephen C. Macevicz*, 07-02845 WHA, U.S. District Court for the Northern District of California Jul. 17, 2008.
Solexa's Opposition to AB's Motion for Summary Judgment of Non-Infringement, dated Jul. 31, 2008, in the matter of *Applera Corp.,—Applied Biosystems Group v. Illumina, Inc., Solexa Inc.*, and *Stephen C. Macevicz*, 07-02845 WHA, U.S. District Court for the Northern District of California.
Declaration of Keith C. Backman in Support of Solexa's Opposition to AB's Motion for Summary Judgment of Noninfringement, dated Jul. 31, 2008, in the matter of *Applera Corp.,—Applied Biosystems Group v. Illumina, Inc., Solexa Inc.*, and *Stephen C. Macevicz*, 07-02845 WHA, U.S. District Court for the Northern District of California.
Expert Statement of Keith C. Backman, Ph.D. regarding Infringement, dated Jul. 31, 2008, in the matter of *Applera Corp.,—Applied Biosystems Group v. Illumina, Inc., Solexa Inc.*, and *Stephen C. Macevicz*, 07-02845 WHA, U.S. District Court for the Northern District of California.
Declaration of Cullen N. Pendleton in Support of Solexa's Opposition to AB's Motion for Summary Judgment of Non-Infringement, dated Aug. 1, 2008, in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit A to Pendleton Declaration (Deposition Transcript of Gina Costa dated May 20, 2008), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit B to Pendleton Declaration (Amendment dated Oct. 16, 1996), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit C to Pendleton Declaration (Deposition Transcript of Keith Backman, Ph.D. dated Jun. 27, 2008), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit D to Pendleton Declaration (SOLiDTM Experiment Tracking System (SETS) Software Dec. 5, 2006.
Exhibit E to Pendleton Declaration (Example 2: What is the sequence of these color signals?), in the matter of *Applera Corp.,—Applied Biosystems Group v. Illumina, Inc., Solexa Inc.*, and *Stephen C. Macevicz*, 07-02845 WHA, U.S. District Court for the Northern District of California Dec. 5, 2006.
Exhibit G to Pendleton Declaration (Sequencing Possibilities), in the matter of *Applera Corp.,—Applied Biosystems Group v. Illumina, Inc., Solexa Inc.*, and *Stephen C. Macevicz*, 07-02845 WHA, U.S. District Court for the Northern District of California Dec. 5, 2006.
Exhibit H to Pendleton Declaration (2 Base Pair Encoding using 4 Dyes), in the matter of *Applera Corp.,—Applied Biosystems Group v. Illumina, Inc., Solexa Inc.*, and *Stephen C. Macevicz*, 07-02845 WHA, U.S. District Court for the Northern District of California Dec. 5, 2006.
Exhibit I to Pendleton Declaration (SOLiD: 2-base encoding), in the matter of *Applera Corp.,—Applied Biosystems Group v. Illumina, Inc., Solexa Inc.*, and *Stephen C. Macevicz*, 07-02845 WHA, U.S. District Court for the Northern District of California Dec. 5, 2006.
Exhibit J to Pendleton Declaration (2 Base Encoding), in the matter of *Applera Corp.,—Applied Biosystems Group v. Illumina, Inc.,*

(56) References Cited

OTHER PUBLICATIONS

*Solexa Inc.*, and *Stephen C. Macevicz*, 07-02845 WHA, U.S. District Court for the Northern District of California Dec. 5, 2006.
Exhibit K to Pendleton Declaration (Sequencing *E. coli*: Finding SNPs), in the matter of *Applera Corp.,—Applied Biosystems Group v. Illumina, Inc., Solexa Inc.*, and *Stephen C. Macevicz*, 07-02845 WHA, U.S. District Court for the Northern District of California Aug. 7, 2008.
Exhibit L to Pendleton Declaration (Amendment dated Nov. 3, 1998), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit M to Pendleton Declaration (Office Action dated Aug. 8, 1998), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Applera Corp.—Applied Biosystems Group's Opposition to Solexa's Motion for Partial Summary Judgment of Infringement, dated Jul. 31, 2008, in the matter of *Applera Corp.,—Applied Biosystems Group v. Illumina, Inc., Solexa Inc.*, and *Stephen C. Macevicz*, 07-02845 WHA, U.S. District Court for the Northern District of California.
Declaration of Gina Costa, Ph.D. in Support of Applera Corp.—Applied Biosystems Group's Opposition to Solexa's Motion for Partial Summary Judgment of Infringement, dated Jul. 31, 2008, in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit A to Costa Declaration (One Base Encoding Prototype), in the matter of *Applera Corp.,—Applied Biosystems Group v. Illumina, Inc., Solexa Inc.*, and *Stephen C. Macevicz*, 07-02845 WHA, U.S. District Court for the Northern District of California Jul. 31, 2008.
Declaration of Michael L. Metzker, Ph.D., in Support of Applera Corp.—Applied Biosystems Group's Motion for Summary Judgment of Noninfringement, dated Jul. 17, 2008, in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit A to Metzker Declaration (U.S. Pat. No. 5,625,050), in the matter of *Applera Corp.,—Applied Biosystems Group v. Illumina, Inc., Solexa Inc.*, and *Stephen C. Macevicz*, 07-02845 WHA, U.S. District Court for the Northern District of California Jul. 31, 2008.
Exhibit B to Metzker Declaration (Periodic Table: Atomic Properties of the Elements), in the matter of *Applera Corp.,—Applied Biosystems Group v. Illumina, Inc., Solexa Inc.*, and *Stephen C. Macevicz*, 07-02845 WHA, U.S. District Court for the Northern District of California Jul. 31, 2008.
Exhibit C to Metzker Declaration (From Phosphate to Bis(methylene) Sulfone: Non-Ionic Backbone Linkers in DNA, Helvetica Chimica Acta—vol. 85 (2002)), in the matter of *Applera Corp.,—Applied Biosystems Group v. Illumina, Inc., Solexa Inc.*, and *Stephen C. Macevicz*, 07-02845 WHA, U.S. District Court for the Northern District of California Jul. 31, 2008.
Exhibit D to Metzker Declaration (Figures), in the matter of *Applera Corp.,—Applied Biosystems Group v. Illumina, Inc., Solexa Inc.*, and *Stephen C. Macevicz*, 07-02845 WHA, U.S. District Court for the Northern District of California Jul. 31, 2008.
Exhibit E to Metzker Declaration (UK Patent No. GB 2 236 852 B), in the matter of *Applera Corp.,—Applied Biosystems Group v. Illumina, Inc., Solexa Inc.*, and *Stephen C. Macevicz*, 07-02845 WHA, U.S. District Court for the Northern District of California Dec. 29, 2008.
Declaration of Eric C. Pai in Support of Applera Corp.—Applied Biosystems Group's Responsive Claim Construction Brief, dated Jan. 21, 2008, in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit A to Pai Declaration (Deposition Transcript of Stephen Macevicz dated May 8, 2008), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit B to Pai Declaration (Deposition Transcript of Keith Backman dated Jun. 27, 2008), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit C to Pai Declaration (Deposition Transcript of Gerald J. Siuta, Ph.D. dated Jun. 10, 2008), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit D to Pai Declaration (Applied Biosystems Offer Letter to S. Macevicz dated Mar. 17, 1992), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit E to Pai Declaration (Deposition Transcript of Stephen Macevicz dated Nov. 28, 2007), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit F to Pai Declaration (Deposition Transcript of Michael Hunkapiller, Ph.D. dated Feb. 21, 2008), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit G to Pai Declaration (Deposition Transcript of Frank Oaks, Ph.D. dated Jul. 22, 2008), in the matter of Applera Corp.,—*Applied Biosystems Group v. Illumina, Inc., Solexa Inc.*, and *Stephen C. Macevicz*, 07-02845 WHA, U.S. District Court for the Northern District of California.
Exhibit H to Pai Declaration (Stephen Macevicz Release), in the matter of *Applera Corp.,—Applied Biosystems Group v. Illumina, Inc., Solexa Inc.*, and *Stephen C. Macevicz*, 07-02845 WHA, U.S. District Court for the Northern District of California dated Jul. 22, 2008.
Solexa's Reply in Support of its Motion for Partial Summary Judgment of Infringement, dated Aug. 7, 2008, in the matter of *Applera Corp.,—Applied Biosystems Group v. Illumina, Inc., Solexa Inc.*, and *Stephen C. Macevicz*, 07-02845 WHA, U.S. District Court for the Northern District of California.
Declaration of Cullen N. Pendleton in Support of Solexa's Reply in Support of its Motion for Partial Summary Judgment of Infringement, dated Aug. 7, 2008, in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit A to Pendleton Declaration (U.S. Pat. No. 2,043,960), in the matter of *Applera Corp.,—Applied Biosystems Group v. Illumina, Inc., Solexa Inc.*, and *Stephen C. Macevicz*, 07-02845 WHA, U.S. District Court for the Northern District of California Aug. 7, 2008.
Exhibit D to Pendleton Declaration (Deposition Transcript of John Quackenbush dated Jul. 1, 2008), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit E to Pendleton Declaration (Example 2: What is the sequence of these color signals?), in the matter of *Applera Corp.,—Applied Biosystems Group v. Illumina, Inc., Solexa Inc.*, and *Stephen C. Macevicz*, 07-02845 WHA, U.S. District Court for the Northern District of California.
Exhibit F to Pendleton Declaration (SOLiD Data—2 base encoding), in the matter of *Applera Corp.,—Applied Biosystems Group v. Illumina, Inc., Solexa Inc.*, and *Stephen C. Macevicz*, 07-02845 WHA, U.S. District Court for the Northern District of California dated Jul. 1, 2008.
Exhibit G to Pendleton Declaration (Sequencing Possibilities), in the matter of *Applera Corp.,—Applied Biosystems Group v. Illumina, Inc., Solexa Inc.*, and *Stephen C. Macevicz*, 07-02845 WHA, U.S. District Court for the Northern District of California.

(56) References Cited

OTHER PUBLICATIONS

Exhibit H to Pendleton Declaration (2 Base Pair Encoding using 4 Dyes), in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Exhibit I to Pendleton Declaration (SOLiD: 2-base encoding), in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Exhibit J to Pendleton Declaration (2 Base Encoding), in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Exhibit K to Pendleton Declaration (Deposition Transcript of Gerald Siuta, Ph.D. dated Jun. 10, 2008), in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Exhibit N To Pendleton Declaration (Applera Corp.—Applied Biosystems Group's Final Invalidity Contentions), in the matter of *Applera Corp.,—Applied Biosystems Group* v. *Illumina, Inc., Solexa Inc.*, and *Stephen C. Macevicz*, 07-02845 WHA, U.S. District Court for the Northern District of California 411-2008.
Applera Corp.—Applied Biosystems Group's Reply in Support of Motion for Summary Judgment of Noninfringement, dated Aug. 7, 2008, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Declaration of Steve E. Comer in Support of Applera Corp.—Applied Biosystems Group's Reply Motion for Summary Judgment of Noninfringement, dated Aug. 7, 2008, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Exhibit A to Comer Declaration (Deposition of Keith Backman dated Jun. 27, 2008), in the matter of *Applera Corp.,—Applied Biosystems Group* v. *Illumina, Inc., Solexa Inc.*, and *Stephen C. Macevicz*, 0702845 WHA, U.S. District Court for the Northern District of California.
Exhibit B to Comer Declaration (Office Action in Response to communicated filed May 12, 1998), in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Exhibit C to Comer Declaration (Amendment dated Nov. 3, 1998), in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Resubmission of Exhibit B to Pendleton Declaration dated Aug. 7, 2008 (Deposition of Gina Costa), in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Resubmission of Exhibit E to Pendleton Declaration dated Aug. 7, 2008 (Agencourt Bioscience—Supplemental funding request for grant R01 HGO03570), in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Resubmission of Exhibit F to Pendleton Declaration dated Aug. 7, 2008 (AB00147319-AB00147320), in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Resubmission of Exhibit G to Pendleton Declaration dated Aug. 7, 2008 (AB00136587 and AB00136589), in the matter of *Applera Corp.,—Applied Biosystems Group* v. *Illumina, Inc., Solexa Inc.*, and *Stephen C. Macevicz*, 07-02845 WHA, U.S. District Court for the Northern District of California.

Resubmission of Exhibit H to Pendleton Declaration dated Aug. 7, 2008 (AB00276286-AB00276291), in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Resubmission of Exhibit I to Pendleton Declaration dated Aug. 7, 2008 (AB00276276-AB00276279), in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Resubmission of Exhibit J to Pendleton Declaration dated Aug. 7, 2008 (Deposition of Alan J. Cox, Ph.D. on Jun. 24, 2008), in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Plaintiff Applera Corp.—Applied Biosystems Group's Disclosures Pursuant to 35 U.S.C. § 282, dated Aug. 29, 2008, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Applied Biosystems' Trial Brief in Support of Disputed Claim Constructions, dated Dec. 29, 2008, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Declaration of Brian M. Kramer in Support of Applied Biosystems' Trial Brief in Support of Disputed Claim Construction, dated Dec. 29, 2008, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Exhibit A to Kramer Declaration (Expert Rebuttal Statement of Keith C. Backman, Ph.D.), in the matter of *Applera Corp.,—Applied Biosystems Group* v. *Illumina, Inc., Solexa Inc.*, and *Stephen C. Macevicz*, 07-02845 WHA, U.S. District Court for the Northern District of California Dec. 29, 2008.
Exhibit B to Kramer Declaration (U.S. Pat. No. 5,750,341), in the matter of *Applera Corp.,—Applied Biosystems Group* v. *Illumina, Inc., Solexa Inc.*, and *Stephen C. Macevicz*, 07-02845 WHA, U.S. District Court for the Northern District of California Dec. 29, 2008.
Exhibit C to Kramer Declaration (U.S. Pat. No. 6,306,597), in the matter of *Applera Corp.,—Applied Biosystems Group* v. *Illumina, Inc., Solexa Inc.*, and *Stephen C. Macevicz*, 07-02845 WHA, U.S. District Court for the Northern District of California Dec. 29, 2008.
Exhibit D to Kramer Declaration (Expert Rebuttal Statement of John E. Quackenbush, Ph.D.), in the matter of *Applera Corp.,—Applied Biosystems Group* v. *Illumina, Inc., Solexa Inc.*, and *Stephen C. Macevicz*, 07-02845 WHA, U.S. District Court for the Northern District of California Jun. 13, 2008.
Exhibit E to Kramer Declaration (Deposition of Keith Backman dated Jun. 27, 2008), in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Solexa's Responsive Trial Brief Regarding Disputed Claim Constructions, dated Jan. 4, 2009, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Declaration of Cullen N. Pendleton in Support of Solexa's Responsive Trial Brief Regarding Disputed Claim Constructions, dated Jan. 4, 2009, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.
Exhibit A to Pendleton Declaration (U.S. Pat. No. 5,750,341), in the matter of *Applera Corp.,—Applied Biosystems Group* v. *Illumina, Inc., Solexa Inc.*, and *Stephen C. Macevicz*, 07-02845 WHA, U.S. District Court for the Northern District of California Oct. 4, 2007.
Exhibit B to Pendleton Declaration (Invention Disclosure), in the matter of *Applera Corp.,—Applied Biosystems Group* v. *Illumina, Inc., Solexa Inc.*, and *Stephen C. Macevicz*, 07-02845 WHA, U.S. District Court for the Northern District of California Oct. 4, 2007.
Exhibit C to Pendleton Declaration (Feb. 13, 2008 Transcript of Proceedings), in the matter of *Applera Corp.,—Applied Biosystems*

(56) References Cited

OTHER PUBLICATIONS

Group v. Illumina, Inc., Solexa Inc., and Stephen C. Macevicz, 07-02845 WHA, U.S. District Court for the Northern District of California.

Exhibit D to Pendleton Declaration (U.S. Pat. No. 6,306,597), in the matter of *Applera Corp.,—Applied Biosystems Group* v. *Illumina, Inc., Solexa Inc.*, and *Stephen C. Macevicz*, 07-02845 WHA, U.S. District Court for the Northern District of California Oct. 4, 2007.

Exhibit E to Pendleton Declaration (Joint Claim Construction and Prehearing Statement), in the matter of *Applera Corp.,—Applied Biosystems Group* v. *Illumina, Inc., Solexa Inc.*, and *Stephen C. Macevicz*, 07-02845 WHA, U.S. District Court for the Northern District of California Oct. 4, 2007.

Infringement Chart submitted to jury filed by Applied Biosystems, dated Jan. 15, 2009, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.

Exhibit A to Infringement Chart submitted to jury filed by Applied Biosystems (Patents in Suit: Claim 1 of '119, '597, and '341), in the *matter of Applera Corp.,—Applied Biosystems Group* v. *Illumina, Inc., Solexa Inc.*, and *Stephen C. Macevicz*, 07-02845 WHA, U.S. District Court for the Northern District of California Jan. 15, 2009.

Exhibit B to Infringement Chart submitted to jury filed by Applied Biosystems (Patents in Suit: Claim 1 of '341, 119, and '597), in the matter of *Applera Corp.,—Applied Biosystems Group* v. *Illumina, Inc., Solexa Inc.*, and *Stephen C. Macevicz*, 07-02845 WHA, U.S. District Court for the Northern District of California Jan. 15, 2009.

Joint Timeline presented during Second Phase of Trial, dated Jan. 27, 2009, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.

Exhibit A to Joint Timeline (Joint Timeline), in the matter of *Applera Corp.,—Applied Biosystems Group* v. *Illumina, Inc., Solexa Inc.*, and *Stephen C. Macevicz*, 07-02845 WHA, U.S. District Court for the Northern District of California Jan. 27, 2009.

Invalidity Charts submitted to jury filed by Solexa, Inc., dated Jan. 27, 2009, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.

Exhibit A to Invalidity Charts (Patents in Suit: Claim 1 of '597), in the matter of *Applera Corp.,—Applied Biosystems Group* v. *Illumina, Inc., Solexa Inc.*, and *Stephen C. Macevicz*, 07-02845 WHA, U.S. District Court for the Northern District of California Jan. 27, 2009.

Select portions of the trial transcript in *Applera Corp.,—Applied Biosystems Group* v. *Illumina, Inc., Solexa Inc.*, and *Stephen C. Macevicz*, 07-02845 WHA, U.S. District Court for the Northern District of California (testimony of Solexa's technical expert, Dr. Keith Backman), pp. 1543 to 1582, dated Jan. 15, 2009, pp. 1614 to 1697, dated Jan. 16, 2009, and pp. 2231 to 2297, dated Jan. 22, 2009.

Select portions of the trial transcript in *Applera Corp.,—Applied Biosystems Group* v. *Illumina, Inc., Solexa Inc.*, and *Stephen C. Macevicz*, 07-02845 WHA, U.S. District Court for the Northern District of California (testimony of Applied Biosystems's technical expert, Dr. Michael Metzker), pp. 2028 to 2121, dated Jan. 21, 2009, and pp. 2282 to 2291, dated Jan. 22, 2009.

Select portions of the trial transcript in *Applera Corp.,—Applied Biosystems Group* v. *Illumina, Inc., Solexa Inc.*, and *Stephen C. Macevicz*, 07-02845 WHA, U.S. District Court for the Northern District of California (testimony of Dr. Stephen C. Macevicz), pp. 704 to 830, dated Jan. 8, 2009, and pp. 856 to 933, dated Jan. 9, 2009.

Select portions of the trial transcript in *Applera Corp.,—Applied Biosystems Group* v. *Illumina, Inc., Solexa Inc.*, and *Stephen C. Macevicz*, 07-02845 WHA, U.S. District Court for the Northern District of California (testimony of Dr. Frank Oaks), pp. 585 to 605, dated Jan. 7, 2009, and pp. 642 to 698, dated Jan. 8, 2009.

Judge Alsup's claim construction ruling, made at trial, in *Applera Corp.,—Applied Biosystems Group* v. *Illumina, Inc., Solexa Inc.*, and *Stephen C. Macevicz*, 07-02845 WHA, U.S. District Court for the Northern District of California, pp. 1798 to 1802 of the trial transcript, dated Jan. 16, 2009.

Oral Argument before Judge Alsup regarding invalidity in *Applera Corp.,—Applied Biosystems Group* v. *Illumina, Inc., Solexa Inc.*, and *Stephen C. Macevicz*, 07-02845 WHA, U.S. District Court for the Northern District of California, pp. 2301 to 2312 of the trial transcript, dated Jan. 22, 2009.

Final Charge to the Jury and Special Verdict Form, issued by Judge Alsup in *Applera Corp.,—Applied Biosystems Group* v. *Illumina, Inc., Solexa Inc.*, and *Stephen C. Macevicz*, 07-02845 WHA, U.S. District Court for the Northern District of California, dated Jan. 22, 2009.

Memorandum Opinion Re Claim Construction of Claim 1 of the '341 Patent, issued by Judge Alsup in *Applera Corp.,—Applied Biosystems Group* v. *Illumina, Inc., Solexa Inc.*, and *Stephen C. Macevicz*, 07-02845 WHA, U.S. District Court for the Northern District of California, dated Jan. 23, 2009.

Special Verdict for Phase Two, dated Jan. 30, 2009, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.

Applied Biosystems' Notice of Motion and Motion for Judgment as a Matter of Law that Claim 1 of the '119 Patent in Invalid and Inventions Did Not Meet Criteria in Paragraph 2 of Employee Invention Agreement, and Motion for New Trial, dated Feb. 2, 2009, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.

Appendix of Admitted Trial Exhibits and Trial Transcripts cited in Support of Applied Biosystems' Motion for Judgment as a Matter of Law that Claim 1 of '199 Patent is Invalid and Inventions Did Not Meet Criteria in Paragraph 2 of Employee invention Agreement, and Motion for New Trial, dated Feb. 2, 2009, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.

Appendix Item 1 Index of Trial Exhibits and Trial Transcripts in Support of Motion for JMOL1, select portions of the trial transcript, Feb. 2, 2009.

Appendix Item 3 Index of Trial Exhibits and Trial Transcripts in Support of Motion for JMOL1, Trial Exhibit 22, Feb. 2, 2009.

Appendix Item 3 Index of Trial Exhibits and Trial Transcripts in Support of Motion for JMOL, Trial Exhibit 39, Feb. 2, 2009.

Appendix Item 4 Index of Trial Exhibits and Trial Transcripts in Support of Motion for JMOL1, Trial Exhibit 39, Feb. 2, 2009.

Appendix Item 5 Index of Trial Exhibits and Trial Transcripts in Support of Motion for JMOL1, Trial Exhibit 42, Feb. 2, 2009.

Appendix Item 6 Index of Trial Exhibits and Trial Transcripts in Support of Motion for JMOL, Trial Exhibit 43, Feb. 2, 2009.

Appendix Item 7 Index of Trial Exhibits and Trial Transcripts in Support of Motion for JMOL, Except of Trial Exhibit 93, Feb. 2, 2009.

Appendix Item 8 Index of Trial Exhibits and Trial Transcripts in Support of Motion for JMOL, Except of Trial Exhibit 140, Feb. 2, 2009.

Appendix Item 9 Index of Trial Exhibits and Trial Transcripts in Support of Motion for JMOL, Trial Exhibit 164 Feb. 2, 2009.

Appendix Item 10 Index of Trial Exhibits and Trial Transcripts in Support of Motion for JMOL, Trial Exhibit 167 Feb. 2, 2009.

Appendix Item 11 Index of Trial Exhibits and Trial Transcripts in Support of Motion for JMOL, Trial Exhibit 456 Feb. 2, 2009.

Appendix Item 12 Index of Trial Exhibits and Trial Transcripts in Support of Motion for JMOL, Trial Exhibit 457 Feb. 2, 2009.

Appendix Item 13 Index of Trial Exhibits and Trial Transcripts in Support of Motion for JMOL, Trial Exhibit 458 Feb. 2, 2009.

Judgment, dated Feb. 3, 2009, in the matter of *Applera Corp.,—Applied Biosystems Group* v. *Illumina, Inc., Solexa Inc.*, and *Stephen C. Macevicz*, 07-02845 WHA, U.S. District Court for the Northern District of California.

Defendants' Opposition to Plaintiff's Renewed Motion for Judgment as a Matter of Law, dated Feb. 19, 2009, in the matter of *Applera*

(56) References Cited

OTHER PUBLICATIONS

Corp.,—Applied Biosystems Group v. Illumina, Inc., Solexa Inc., and Stephen C. Macevicz, 07-02845 WHA, U.S. District Court for the Northern District of California.

Appendix to Defendants' Oppositions to Plaintiff's Motions for Judgment as a Matter of Law) filed by Stephen C. Macevicz, Illumina, Inc., Solexa Inc., dated Feb. 19, 2009, in the matter of Applera Corp.,—Applied Biosystems Group v. Illumina, Inc., Solexa Inc., and Stephen C. Macevicz, 07-02845 WHA, U.S. District Court for the Northern District of California.

Appendix Item 4 to Opposition filed by Macevicz, Trial Exhibit 42, Feb. 19, 2009.

Appendix Item 5 to Opposition filed by Macevicz, Trial Exhibit 43, Feb. 19, 2009.

Appendix Item 6 to Opposition filed by Macevicz, Trial Exhibit 69, Feb. 19, 2009.

Appendix Item 7 to Opposition filed by Macevicz, Trial Exhibit 140, Feb. 19, 2009.

Appendix Item 8 to Opposition filed by Macevicz, Trial Exhibit 149, Feb. 19, 2009.

Appendix Item 9 to Opposition filed by Macevicz, Trial Exhibit 183, Feb. 19, 2009.

Appendix Item 10 to Opposition filed by Macevicz, Trial Exhibit 342, Feb. 19, 2009.

Appendix Item 11 to Opposition filed by Macevicz, Trial Exhibit 344, Feb. 19, 2009.

Appendix Item 12 to Opposition filed by Macevicz, Trial Exhibit 456, Feb. 19, 2009.

Appendix Item 13 to Opposition filed by Macevicz, Trial Exhibit 457, Feb. 19, 2009.

Appendix Item 14 to Opposition filed by Macevicz, Trial Exhibit 534, Feb. 19, 2009.

Applied Biosystems' Reply in Support of Motion for Judgment as a Matter of Law that Claim 1 of '119 Patent is Invalid and Inventions Did Not Meet Criteria in Paragraph 2 of Employee Invention Agreement, and Motion for New Trial, dated Feb. 26, 2009, in the matter of Applera Corp.,—Applied Biosystems Group v. Illumina, Inc., Solexa Inc., and Stephen C. Macevicz, 07-02845 WHA, U.S. District Court for the Northern District of California.

Supplemental Appendix of Admitted Trial Exhibits and Trial Transcripts Cited in Applied Biosystems' Reply in Support of Motion for Judgment as a Matter of Law that Claim 1 of '119 Patent is Invalid and Inventions Did Not Meet Criteria in Paragraph 2 of Employee Invention Agreement, and Motion for New Trial, dated Feb. 26, 2009, in the matter of Applera Corp.,—Applied Biosystems Group v. Illumina, Inc., Solexa Inc., and Stephen C. Macevicz, 07-02845 WHA, U.S. District Court for the Northern District of California.

Appendix Item 2 Supplemental Appendix of Admitted Trial Exhibits and Trial Transcripts Cited in Applied Biosystems' Reply , Trial Exhibit 3 Feb. 26, 2009.

Appendix Item 2 Supplemental Appendix of Admitted Trial Exhibits and Trial Transcripts Cited in Applied Biosystems' Reply, Trial Exhibit 3 Feb. 26, 2009.

Appendix Item 2 Supplemental Appendix of Admitted Trial Exhibits and Trial Transcripts Cited in Applied Biosystems' Reply, Trial Exhibit 25 dated Feb. 26, 2009.

Appendix Item 3 Supplemental Appendix of Admitted Trial Exhibits and Trial Transcripts Cited in Applied Biosystems' Reply, Trial Exhibit 171 dated Feb. 26, 2009.

Order by Judge Alsup Denying Applied Biosystems's Motion for Judgment as a Matter of Law, dated Mar. 6, 2009, in the matter of Applera Corp.,—Applied Biosystems Group v. Illumina, Inc., Solexa Inc., and Stephen C. Macevicz, 07-02845 WHA, U.S. District Court for the Northern District of California.

Notice of Appeal as to Jury Verdict, Judgment, Order on Motion for Judgment as a Matter of Law, by Applera Corporation—Applied Biosystems Group, dated Mar. 9, 2009, in the matter of Applera Corp.,—Applied Biosystems Group v. Illumina, Inc., Solexa Inc., and Stephen C. Macevicz, 07-02845 WHA, U.S. District Court for the Northern District of California.

Special Verdict, in the matter of Applera Corp.,—Applied Biosystems Group v. Illumina, Inc., Solexa Inc., and Stephen C. Macevicz, 07-02845 WHA, U.S. District Court for the Northern District of California Jan. 30, 2009.

Solexa's Amended Notice of Appeal, dated Apr. 6, 2009, in the matter of Applera Corp.,—Applied Biosystems Group v. Illumina, Inc., Solexa Inc., and Stephen C. Macevicz, 07-02845 WHA, U.S. District Court for the Northern District of California.

Joint Stipulation and Order Regarding Infringement and Invalidity of the '597 Patent, dated Jan. 26, 2009, in the matter of Applera Corp.,—Applied Biosystems Group v. Illumina, Inc., Solexa Inc., and Stephen C. Macevicz, 07-02845 WHA, U.S. District Court for the Northern District of California.

Exhibit A to Joint Stipulation and Order Regarding Infringement and Invalidity of the '597 Patent (Judge Alsup's construction of certain tern in claim 1 of the '597 patent), dated Jan. 22, 2009, in the matter of Applera Corp.,—Applied Biosystems Group v. Illumina, Inc., Solexa Inc., and Stephen C. Macevicz, 07-02845 WHA, U.S. District Court for the Northern District of California.

Opening Brief of Plaintiff—Appellant Applera Corporation—Applied Biosystems Group, dated Jun. 12, 2009, in the matter of Applera Corp.,—Applied Biosystems Group v. Illumina, Inc., Solexa Inc., and Stephen C. Macevicz, Appeal Nos. 2009-1253, -1260, United States Court of Appeals for the Federal Circuit.

Response Brief of Defendants—Appellees Illumina, Inc. and Stephen C. Macevicz and Opening Brief of Cross-Appellant Solexa, Inc., dated Jul. 22, 2009, in the matter of Applera Corp.,—Applied Biosystems Group v. Illumina, Inc., Solexa Inc., and Stephen C. Macevicz, Appeal Nos. 2009-1253, -1260, United States Court of Appeals for the Federal Circuit.

Federal Circuit Opinion decided Mar. 25, 2010, in the matter of Applera Corp.,—Applied Biosystems Group v. Illumina, Inc., Solexa Inc., and Stephen C. Macevicz, Appeal Nos. 2009-1253, -1260, United States Court of Appeals for the Federal Circuit.

U.S. Appl. No. 09/266,187 as filed, dated Mar. 27, 2000.

File History for U.S. Pat. No. 6,855,523, dated May 14, 2010.

File History for U.S. Appl. No. 08/263,937 dated May 14, 2010.

File History for U.S. Appl. No. 08/344,203 dated May 14, 2010.

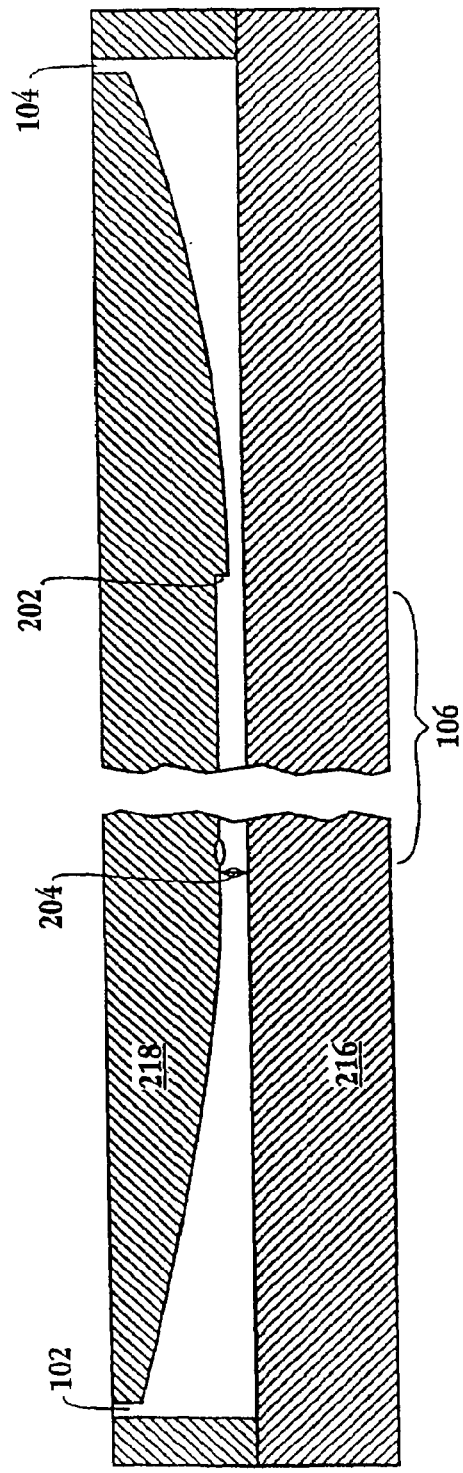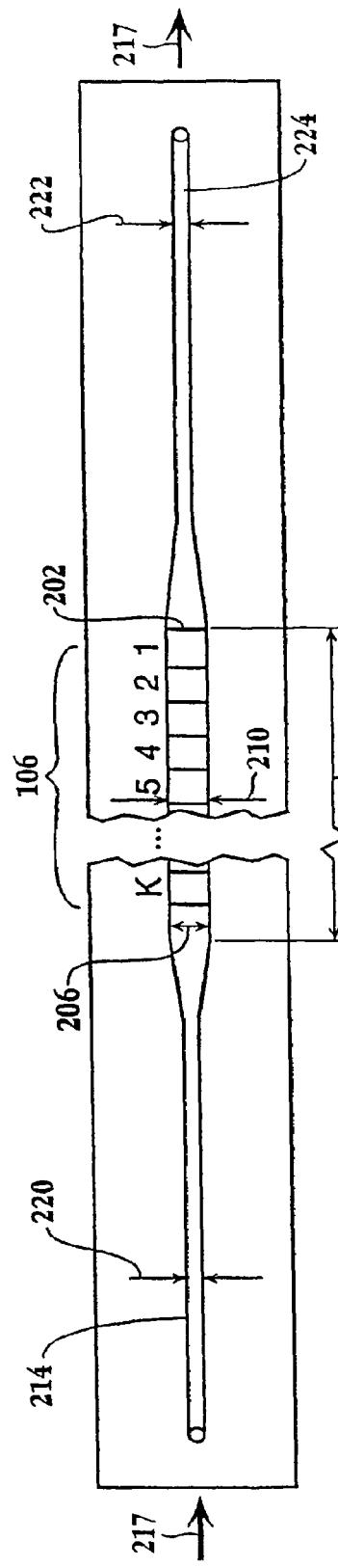

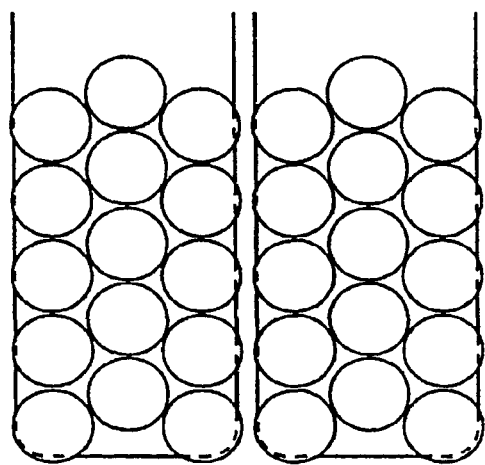 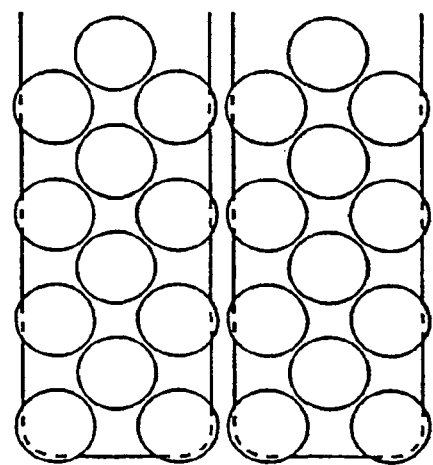
Fig. 3A          Fig. 3B
 
Fig. 3C          Fig. 3D

SEQUENCE LISTING

```
<160> NUMBER OF SEQ ID NOS: 20

<210> SEQ ID NO 1
<211> LENGTH: 78
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(78)
<223> OTHER INFORMATION: n = A, T, C, or G
```

<400> SEQUENCE: 1
actaatcgtc tcactattta attaannnnn nnnnnnnnnn nnnnnnnnnn nnnnnnncct    60
tttttttttt tttttttv                                                  78

<210> SEQ ID NO 2
<211> LENGTH: 17
<212> TYPE: DNA
<213> ORGANISM: Artificial Sequence
<220> FEATURE:
<223> OTHER INFORMATION: synthetic fragment

<400> SEQUENCE: 2 atagggtct tcggtac                                                    17

<210> SEQ ID NO 3
<211> LENGTH: 19
<212> TYPE: DNA
<213> ORGANISM: Artificial Sequence
<220> FEATURE:
<223> OTHER INFORMATION: synthetic cleavage adaptor

<400> SEQUENCE: 3
gatcagctgc tgcaaattt                                                 19

<210> SEQ ID NO 4
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 4
annntacagc tgcatccctt ggcgctgagg                                     30

<210> SEQ ID NO 5
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 5
nanntacagc tgcatccctg ggcctgtaag                                     30

<210> SEQ ID NO 6
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 6
cnnntacagc tgcatccctt gacgggtctc                                     30

```
<210> SEQ ID NO 7
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 7
ncnntacagc tgcatccctg cccgcacagt                                    30

<210> SEQ ID NO 8
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 8
gnnntacagc tgcatcccTT cgcctcggac                                    30

<210> SEQ ID NO 9
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 9
ngnntacagc tgcatccctg atccgctagc                                    30

<210> SEQ ID NO 10
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 10
tnnntacagc tgcatcccTT ccgaacccgc                                    30

<210> SEQ ID NO 11
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 11
ntnntacagc tgcatccctg aggggatag                                     30
```

```
<210> SEQ ID NO 12
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 12
nnantacagc tgcatccctt cccgctacac                                              30

<210> SEQ ID NO 13
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 13
nnnatacagc tgcatccctg actccccgag                                              30

<210> SEQ ID NO 14
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 14
nncntacagc tgcatccctg tgttgcgcgg                                              30

<210> SEQ ID NO 15
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 15
nnnctacagc tgcatccctc tacagcagcg                                              30

<210> SEQ ID NO 16
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 16
```

```
nngntacagc tgcatccctg tcgcgtcgtt                                               30

<210> SEQ ID NO 17
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 17
nnngtacagc tgcatccctc ggagcaacct                                               30

<210> SEQ ID NO 18
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 18
nntntacagc tgcatccctg gtgaccgtag                                               30

<210> SEQ ID NO 19
<211> LENGTH: 30
<212> TYPE: DNA
<213> ORGANISM: Artificial Sequence
<220> FEATURE:
<223> OTHER INFORMATION: synthetic encoded adaptor
<220> FEATURE:
<221> NAME/KEY: misc_feature
<222> LOCATION: (1)...(30)
<223> OTHER INFORMATION: n = A, T, C or G

<400> SEQUENCE: 19
nnnttacagc tgcatccctc ccctgtcgga                                               30

<210> SEQ ID NO 20
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 20
atgcacgcgt aggg                                                                14
```

SYSTEM AND APPARATUS FOR SEQUENTIAL PROCESSING OF ANALYTES

CROSS-REFERENCE TO RELATED APPLICATIONS

This application is a continuation of U.S. application Ser. No. 13/693,658, filed on Dec. 4, 2012 which is a continuation of U.S. application Ser. No. 11/974,239, filed on Oct. 12, 2007, now U.S. Pat. No. 8,361,713, which is a division of U.S. application Ser. No. 11/207,443 filed on Aug. 18, 2005, now U.S. Pat. No. 7,282,370, which is a division of U.S. application Ser. No. 09/908,131 filed on Jul. 17, 2001, now U.S. Pat. No. 6,969,488, which is a division of U.S. application Ser. No. 09/424,028 filed on Nov. 16, 1999, now U.S. Pat. No. 6,406,848, which is a 371 of PCT Application No. PCT/US98/11224 filed on May 22, 1998, all of which are incorporated herein by reference in their entireties.

REFERENCE TO SEQUENCE LISTING

The present application is being filed with a Sequence Listing in electronic format. The Sequence Listing is provided as a file entitled ILLINC153C3.TXT created Apr. 4, 2014, which is approximately 5 KB in size. The information in the electronic format of the Sequence Listing is incorporated herein by reference in its entirety.

FIELD OF THE INVENTION

The invention relates generally to systems and apparatus for carrying out large scale parallel reactions on solid phase supports, and more particularly, to systems and apparatus for monitoring and carrying out reactions on arrays of microparticles.

BACKGROUND

The desire to understand and analyze complex chemical and biological systems has led to the development of analytical techniques that employ parallelization and miniaturization of analyte processing, e.g. Graber et al., Current Opinion in Biotechnology, 9:14-18 (1998); Fodor et al., Nature, 364: 555-556 (1993); Meier-Ewert et al., Nature, 361:375-376 (1993); Taylor et al., Nucleic Acids Research, 25:3164-3168 (1997); Garner et al., BioTechniques, 14:112-115 (1993); Lam et al., Nature, 354:82-84 (1991); Ohlmeyer et al., Proc. Natl. Acad. Sci., 90:10922-10926 (1993); DeRisi et al., Science, 278:680-686 (1997); Wodicka et al., Nature Biotechnology, 15:1359-1367 (1997); and the like.

Many of these techniques employ microparticles for synthesizing analytes or for capturing analytes for subsequent analysis, e.g. Lam et al. (cited above); Benkovic et al., International patent application PCT/US95/03355; Gavin et al., International patent application PCT/EP97/02039; Brenner et al., International patent application PCT/US96/09513, and the like. Even though the properties of different types of microparticles can vary widely, microparticles generally facilitate the construction and manipulation of large repertoires of analytes with minimal reagent and/or sample consumption. However, handling and manipulating large numbers of microparticles, e.g. tens to hundreds of thousands, for carrying out specific chemical and/or biochemical analyses gives rise to many difficulties, including whether sufficient signal is generated on individual microparticles for detection, how to track individual microparticles through multiple steps of a process, mechanical strength of microparticles under pressure or flow conditions, the ability to uniformly deliver reagents to microparticles for carrying out steps of an analytical process, whether clumping or other inappropriate interaction of microparticles and/or reagents occurs, whether or adsorption of analytes and/or processing reagents onto vessel walls occurs, whether protein reagents or analytes denature causing a disruption of reagent distribution and access, whether adjacent microparticles will interact, e.g. to degrade or obscure a signal or to inhibit reagent access, and the like.

In view of these difficulties, it would be desirable to provide a system and apparatus for handling and processing multiple solid phase supports, such as populations of microparticles. It would be especially desirable if such system and apparatus permitted the tracking and analysis of multiple analytes anchored to separate microparticles through a sequence of several processing and/or analysis steps.

SUMMARY OF THE INVENTION

Accordingly, objects of our invention include, but are not limited to, providing a system and apparatus for sequentially delivering reagents to a population of analytes anchored to a separate microparticles; providing an apparatus for simultaneously monitoring the interactions of processing reagents and analytes on the surfaces of microparticles disposed in a planar array; providing an apparatus for detecting optical signals generated by, or as the result of, interactions of processing reagents and analytes on the surfaces of microparticles disposed in a planar array; providing an apparatus for detecting pluralities of optical signals, each such plurality being generated at the surface of the same microparticle as a result of interactions between processing reagents and an analyte anchored to the surface of such microparticle; providing an apparatus for simultaneously tracking the positions of individual microparticles in a population of microparticles disposed in a flow chamber as a closely packed planar array; and providing a system and apparatus for simultaneously analyzing the nucleotide sequences of a population of polynucleotides anchored to microparticles disposed in a planar array in a flow chamber.

Our invention achieves these and other objects with an apparatus comprising a flow chamber for disposing a population of microparticles in a planar array; fluidic means for sequentially delivering processing reagents from one or more reagent reservoirs to the flow chamber; and detection means for detecting a sequence of optical signals from each of the microparticles of the population. Preferably, the sequences of optical signals are generated as a result of a multi-step analytical process, such as nucleic acid sequence analysis.

In one aspect, the invention provides a system for simultaneously monitoring a population of analytes which includes the apparatus of the invention, microparticles carrying the analytes, and software means for processing images of, and/or optical signals generated by, the microparticles when disposed in a planar array. Preferably, the flow chamber includes constraining means for restricting the movement of microparticles during cycles of reagent delivery.

In another aspect, the invention includes a system for simultaneously analyzing the nucleotide sequences of a population of polynucleotides. Copies of each kind of polynucleotide in the population are sorted onto and anchored to one or more microparticles so that a population of loaded microparticles is formed. Loaded microparticles are disposed in a planar array in a flow chamber through which processing reagents are sequentially delivered to the loaded microparticles from one or more reagent reservoirs by a fluidic means.

Optical signals generated by, or produced as a result of, the interaction of processing reagents and polynucleotides on the microparticles are imaged by a detection means. Preferably, when analysis includes determining the nucleotide sequence of a portion of each polynucleotide on the different microparticles, massively parallel signature sequencing (MPSS) analysis is employed, e.g. as described in Albrecht et al, International patent application PCT/US97/09472.

BRIEF DESCRIPTION OF THE DRAWINGS

FIG. 2a is bilateral cut away view of a flow chamber.

FIG. 2b is a top view of a flow chamber.

FIGS. 3a, 3b, 3c, and 3d schematically illustrate microparticle constraining means for a flow chamber.

DEFINITIONS

Figure 1A:
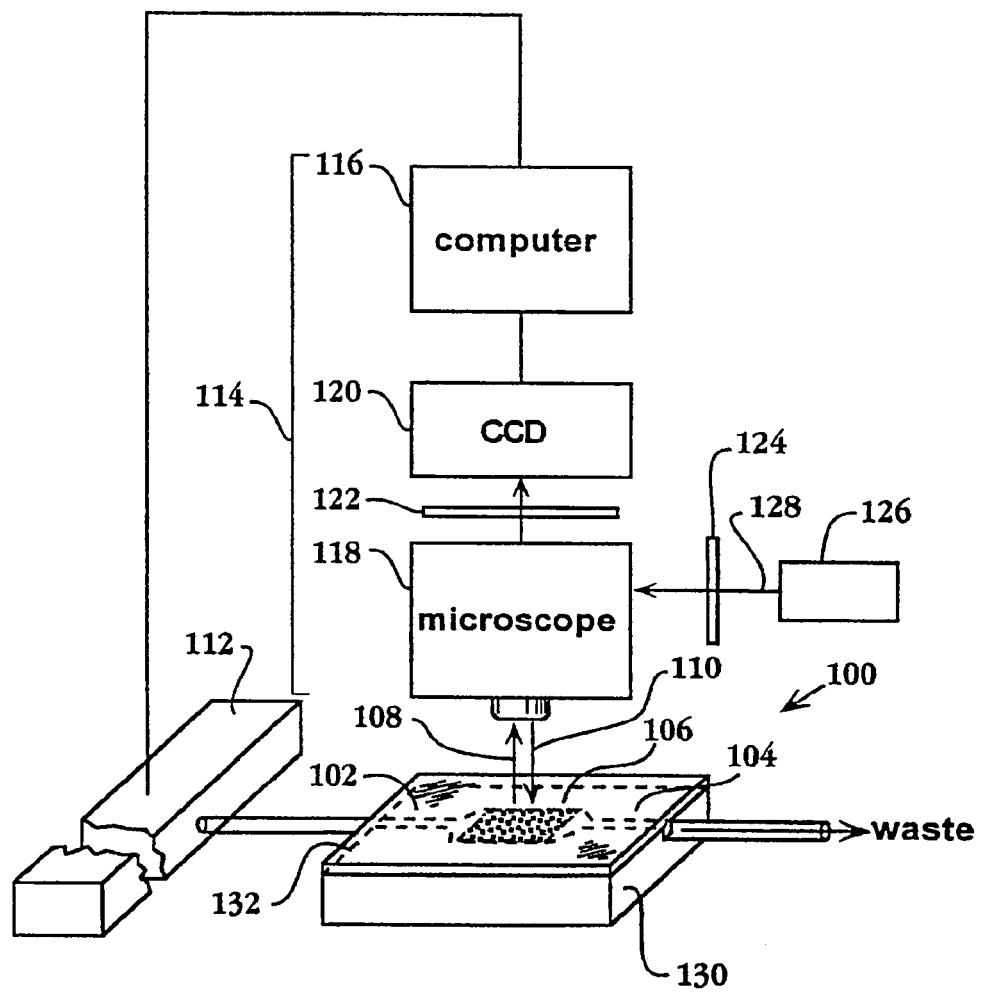
FIG. 1a is a schematic representation of a flow chamber and fluidics and detection systems for observing a planar array of microparticles loaded with analyte molecules, such as cDNA molecules for sequencing.

"Complement" or "tag complement" as used herein in reference to oligonucleotide tags refers to an oligonucleotide to which a oligonucleotide tag specifically hybridizes to form a perfectly matched duplex or triplex. In embodiments where specific hybridization results in a triplex, the oligonucleotide tag may be selected to be either double stranded or single stranded. Thus, where triplexes are formed, the term "complement" is meant to encompass either a double stranded complement of a single stranded oligonucleotide tag or a single stranded complement of a double stranded oligonucleotide tag.

The term "oligonucleotide" as used herein includes linear oligomers of natural or modified monomers or linkages, including deoxyribonucleosides, ribonucleosides, anomeric forms thereof, peptide nucleic acids (PNAs), and the like, capable of specifically binding to a target polynucleotide by way of a regular pattern of monomerto-monomer interactions, such as Watson-Crick type of base pairing, base stacking, Hoogsteen or reverse Hoogsteen types of base pairing, or the like. Usually monomers are linked by phospho diester bonds or analogs thereof to form oligonucleotides ranging in size from a few monomeric units, e.g. 3-4, to several tens of monomeric units, e.g. 40-60. Whenever an oligonucleotide is represented by a sequence of letters, such as "ATGCCTG," it will be understood that the nucleotides are in 5'□3' order from left to right and that "A" denotes deoxyadenosine, "C" denotes deoxycytidine, "G" denotes deoxyguanosine, and "T" denotes thymidine, unless otherwise noted. Usually oligonucleotides of the invention comprise the four natural nucleotides; however, they may also comprise non-natural nucleotide analogs. It is clear to those skilled in the art when oligonucleotides having natural or non-natural nucleotides may be employed, e.g. where processing by enzymes is called for, usually oligonucleotides consisting of natural nucleotides are required.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

As used herein, "nucleoside" includes the natural nucleosides, including 2'-deoxy and 2'-hydroxyl forms, e.g. as described in Kornberg and Baker, DNA Replication, $2^{nd}$ Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90:543-584 (1990), or the like, with the only proviso that they are capable of specific hybridization. Such analogs include synthetic nucleosides designed to enhance binding properties, reduce complexity, increase specificity, and the like.

As used herein "sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, as well as the express identification and ordering of nucleosides, usually each nucleoside, in a target polynucleotide. The term also includes the determination of the identification, ordering, and locations of one, two, or three of the four types of nucleotides within a target polynucleotide. For example, in some embodiments sequence determination may be effected by identifying the ordering and locations of a single type, of nucleotide, e.g. cytosines, within the target polynucleotide "CATCGC..." so that its sequence is represented as a binary code, e.g. "100101..." for "C-(not C)-(not C)-C-(not C)-C..." and the like.

As used herein, the term "complexity" in reference to a population of polynucleotides means the number of different species of molecule present in the population.

DETAILED DESCRIPTION OF THE INVENTION

The system and apparatus of the invention is particularly applicable to the analysis of molecules that can be anchored in populations of duplicate copies to particulate solid phase supports. That is, in accordance with the invention, each analyte of a population is present on at least one microparticle in a quantity sufficient for the type of analysis being performed. For example, if combinatorially synthesized peptides on the microparticles are screened against a soluble receptor protein for detecting those that form stable complexes, the number of peptides available for binding on the surface of the microparticles must be large enough to generate a detectable signal when a binding event occurs. Of course, many additional factors well known in the art will present additional design constraints, such as the nature of the system for generating optical signals, the concentration of receptors, pH, salt concentration, the density and accessibility of the peptides on the microparticle surface, the solvent system employed, and the like. Analyte populations particularly relevant for use with the present apparatus include combinatorial libraries synthesized on microparticle supports, e.g as disclosed in Lam et al., Chem. Rev., 97:411-448 (1997); or Dower et al., U.S. Pat. No. 5,708,153, and polynucleotide libraries sorted onto microparticle supports, e.g. as disclosed in Brenner (cited above).

FIG. 1A is a schematic representation of an embodiment of the invention for detecting fluorescent signals. Flow chamber (100) having inlet (102), outlet (104) and planar cavity (106) holds microparticles in a planar array from which optical signals (108) generated by analytes and/or reactants on microparticles can be collected and imaged. Flow chamber (100) is operationally associated with fluidic system (112) and detection system (114), so that delivery of fluids and collection of signals is under control of computer (116). Preferably, optical signals are collected by microscope (118) and are imaged onto a solid state imaging device, such as charge-coupled device (CCD) (120) which is capable of generating a digital image of the physical image of the microparticle array with sufficient resolution for individual microparticles to be distinguished. For fluorescent signals, detection system (114) usually includes appropriate bandpass filter (122) for optical signal (108), bandpass filter (124) for excitation beam (128) generated by light source (126), and other standard components. As illustrated, a conventional fluorescence microscope is preferred which is configured for epiillumination. There is a great deal of guidance in the art for selecting appropriate fluorescence microscopes, e.g Wang and Taylor, editors, Fluroescence Microscopy of Living Cells in Culture, Parts A and B, Methods in Cell Biology, Vols. 29 and 30 (Academic Press, New York, 1989).

A key feature of the invention is flow chamber (100). Body (130) of flow chamber (100) preferably comprised inlet (102), outlet (104) and planar cavity (106) which are formed by standard micromachining techniques, e.g. Ekstrom et al., International patent application PCT/SE91/00327; Brown, U.S. Pat. No. 4,911,782; Harrison et al, Anal. Chem. 64:1926-1932 (1992); and the like. Transparent plate (132) is sealingly attached to body (130) to form an operational flow chamber (100). Body (130) may be constructed from several different materials including glass, silicon, polyethylene, polyester, teflon, other plastics, and the like. Preferably, transparent plate (132) is glass or quartz; and, when body (130) and transparent plate (132) are glass or silicon, transparent plate (132) is preferably attached to body (130) by anodic bonding, e.g. Pomerantz, U.S. Pat. No. 3,397,279. Key functions of the flow chamber include i) holding a population of microparticles in a substantially immobilized planar array, or monolayer, during a sequence of processing steps, ii) ensuring that processing reagents can access each microparticle during each step of a process, and iii) minimizing processing reagent usage. The degree of immobilization required may vary among different embodiments. Generally, more movement of microparticles within a planar array increases the computational and measurement burden of tracking positions of microparticles by image processing software. Design tradeoffs therefore exist between the use of image processing software and the use of physical and/or chemical means for constraining microparticle movement. Preferably, physical and/or chemical means are employed to constrain microparticle movement within the planar array of micro particles in flow chamber (100). Such means are referred to herein as "movement constraining means." Most preferably, physical, or mechanical, movement constraining means are employed.

Preferably, microparticles are disposed in flow chamber (100) in a closely packed planar array. As used herein, "closely packed" in reference to a planar array means either that the number of microparticles per unit area of a planar array is at least eighty percent of the number of micro particles in a hexagonal array of equal area, or that the average distance between centers of adjacent microparticles is less than two microparticle diameters. As used herein, a "hexagonal" array of microparticles means a planar array of microparticles in which every microparticle in the array contacts at least six other adjacent microparticles, as shown in FIG. 3A.

Figure 2C:
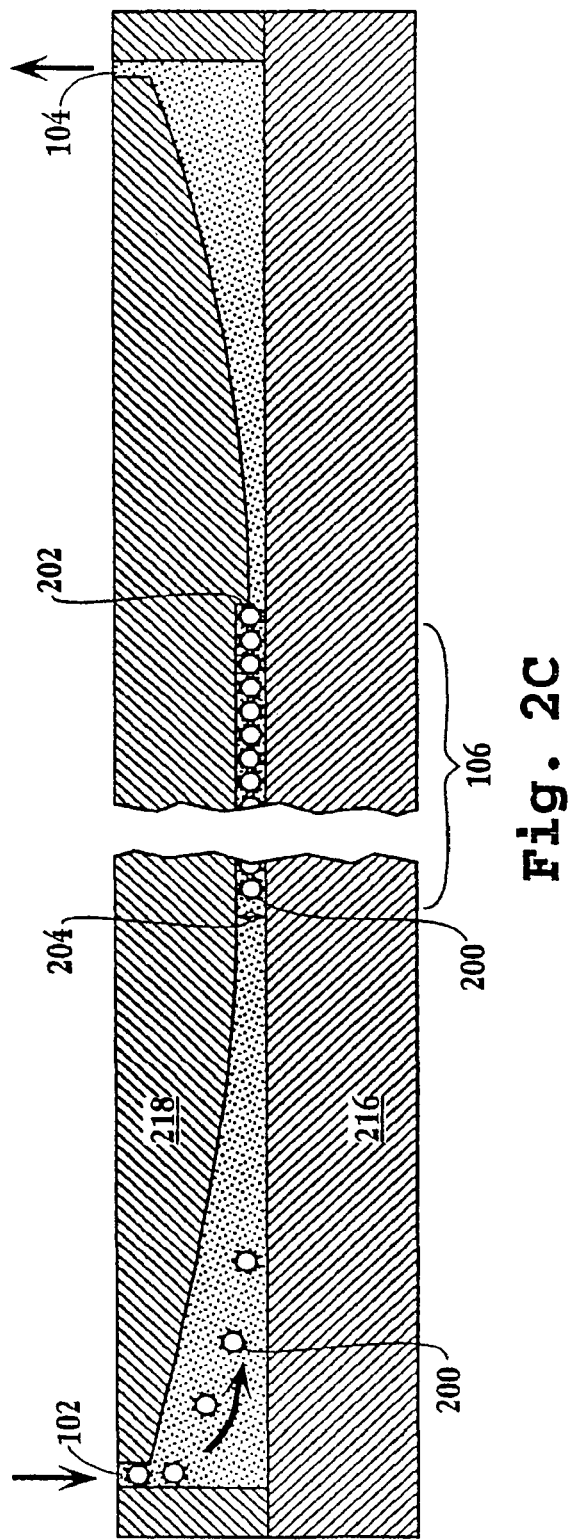
FIG. 2c is an illustration of microparticles being loaded into a flow chamber.

Additional features of flow chamber (100) of a preferred embodiment are illustrated in FIGS. 2A through 2C. FIG. 2A is a cross sectional view along a longitudinal plane that bisects flow chamber (100). The same view, in a more abstracted rendition, is shown in FIG. 2C. In both Figures, inlet (102) fluidly communicates with planar cavity (106) and outlet (104). Microparticles (200) carrying analytes enter inlet (102) and are carried by a suspending buffer to planar cavity (106) where they become packed against dam (202) which prevents the microparticles from exiting the flow chamber through outlet (104). Structurally, dam (202) may be formed by a sudden reduction of the vertical dimension of planar cavity (106). Preferably, vertical dimension (204) of planar cavity (106) is selected so that microparticles (200) are constrained to a plane, i.e. a monolayer, when they pack against dam (202). More preferably, vertical dimension (204) is selected to be between about 120 to 150 percent of the diameter of the microparticles employed. For example, when microparticles are employed that have diameters of 5 µm, vertical dimension (204) may be 7 µm. Magnetic microparticles may be constrained to a plane and constrained from movement by applying a magnetic field so that the microparticles are attracted to the ceiling or to the floor of planar cavity (106). Width (206) of planar cavity (106) is not a critical dimension; however, for convenience and efficiency, width (206) may be selected to correspond to the dimensions of the signal collection region of detection system (114). Such regions labeled 1 through k in FIG. 2B are referred to herein as "tiles." That is, the region of planar cavity (106) occupied by microparticles may be divided into non-overlapping areas, referred to as "tiles," that cover the entire occupied region. FIG. 2B, which is a top view of the flow chamber of FIG. 2A, also shows inlet (102), planar cavity (106), dam (202), and outlet (104) that lie in sequence along axis (217) of flow chamber (100).

Many movement constraining means may be selected for use with the flow chamber, either alone or in combination. Such means include loading microparticles with trace amounts of a chemically reactive species which may be activated and cross-linked; providing physical, or mechanical, structures, such as ridges, within the flow chamber; providing magnetically responsive microparticles which may be immobilized by an external magnetic field; providing a second population of microparticles that are loaded into a flow chamber after the analyte-containing population, which forces the analyte containing population against dam (202); and the like. Exemplary chemically reactive species for use with nucleic acid analytes are disclosed in Summerton et al., U.S. Pat. No. 4,123,610; Gamper et al., J. Mol. Biol., 197:349-362 (1987); Hearst, Ann. Rev. Phys. Chem. 39:291-315 (1988); Pieles et al., Nucleic Acids Research, 17:8967-8978 (1989); and the like.

Preferably, microparticle movement is constrained by providing a flow chamber with planar cavity (106) containing a plurality of ridges running parallel to axis (217) of the flow chamber, i.e. parallel to the direction of reagent flow, so that microparticles are arranged into rows, which may be single-file, or several microparticles wide, as shown in FIGS. 3A, 3B, 3C, and 3D. The particular selection may depend on several factors, including the degree of immobilization desired, constraints imposed by the fabrication technique used to construct the flow chamber, the amount of reagent access desired, the degree to which flow resistance or back-pressure can be tolerated, and the like. FIGS. 3A and 3B illustrate two possible distances between parallel ridges. In FIG. 3A, the distance is selected to permit maximal packing of micro particles into a hexagonal array, and in FIG. 3B, the distance is selected for less efficient packing, but for increased reagent access to microparticle surfaces.

In some embodiments, such as those employing enzymatic processes, the inner surfaces of flow chamber (100) may be passivated, that is, treated to render such surfaces inert and/or non-adsorbing with respect to enzymes. The type of treatment depends on the sensitivity of the enzymes used in the process, and their affinity for the surfaces. Surface treatments include silanization, e.g. with commercially available reagents (Pierce, Rockford, Ill.); and/or adsorption of various blocking polymers, such as poly-a-alanine, polyglycine, polyadenylic acid, polymaleimide, polyvinylpyrrolidone, or the like, e.g. Shoffner et al., Nucleic Acids Research, 24:375-379 (1996). Preferably, glass inner surfaces of flow chamber (100) are covalently coated with a neutral coating, such as allyl methacrylate, using the technique disclosed in Sandoval et al., U.S. Pat. No. 5,326,738, which is incorporated by reference.

Figure 1B:
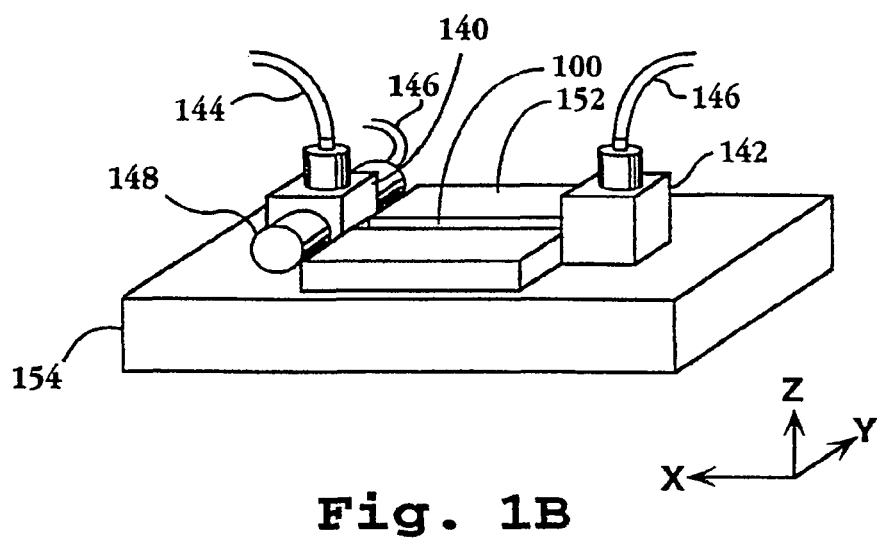
FIG. 1b is a schematic of a preferred holder for a flow chamber.

FIG. 1B illustrates flow chamber (100) mounted between holders (140) and (142) which sealingly connect inlet (102) to inlet tubing (144) and outlet (104) to outlet tubing (146), respectively. Preferably, holder (140) contains a rotary valve (not shown) operated by actuator (148) that shunts fluid flowing through inlet tubing (144) to inlet (102) or to waste line (150). Such a valve minimizes the amount of process reagent from a previous step that must be passed through flow chamber (100) prior to the initiation of the next process step. That is, such a rotary valve permits reagent in inlet tubing (144) to be shunted to waste and replaced by processing reagent required for the next step in the process being executed. Preferably, for use in DNA analysis, peltier block (152) is employed to control temperature in flow chamber (100) and the entire assembly including flow chamber (100) and peltier block (152) is mounted on xyz-stage (154) which is under control of computer (116).

Figure 4:
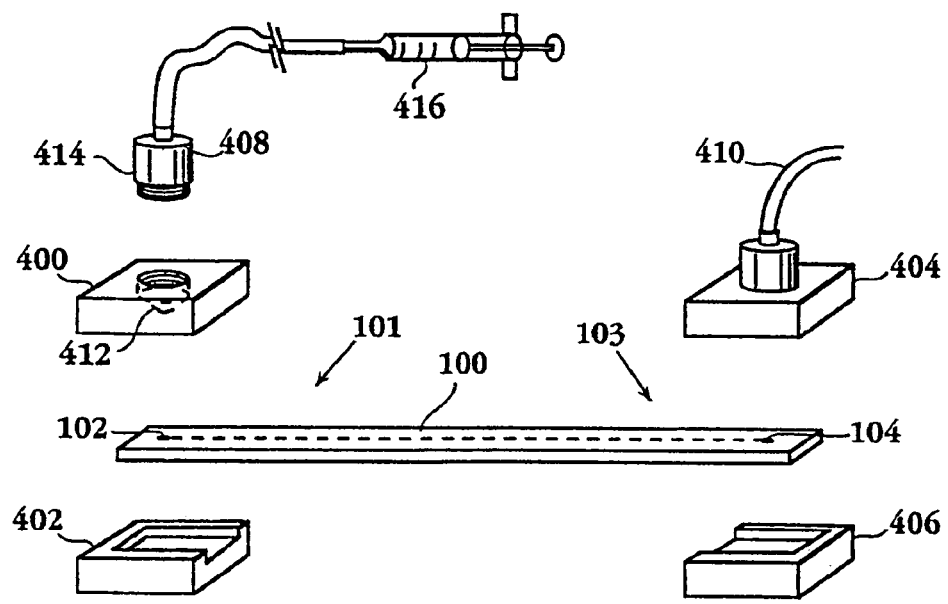
FIG. 4 is a schematic representation of a device for loading microparticles into a flow chamber.

Preferably, microparticles are loaded into flow chamber (100) prior to attachment of holders (140) and (142) and the initiation of processing steps. FIG. 4 illustrates a microparticle loader for loading microparticles into flow chamber (100). Flow chamber (100) is mounted between holders (400), (402), (404), and (406). Holders (400) and (402) sealingly clamp onto the inlet end (101) of flow chamber (100) and holders (404) and (406) sealingly clamp onto the outlet end (103) of flow chamber (100) so that inlet tubing (408) is in fluid communication with outlet tubing (410) when the microparticle loader is assembled. Inlet tubing (408) is connected to syringe (416) which is used to drive fluid through flow chamber (100). Holder (400) is constructed to have conical passage (412) which narrows to match the diameter of inlet (102) of flow chamber (100). After assembly of holders (400), (402), (404), and (406) a suspension of micro particles is placed in the conical passage after which fitting (414) is sealingly connected to holder (400). Fluid pressure and flow generated by syringe (416) then drives the microparticles into planar cavity (106) and against dam (202). In a preferred embodiment which employs 5 μm diameter GMA microparticles carrying DNA, approximately 500 thousand microparticles are loaded into flow chamber (100) by placing 5 μL of a 100 thousand microparticle/μL solution (TE buffer, pH 8.0, Sambrook et al., Molecular Cloning, Second Edition (Cold Spring Harbor Laboratory, New York, 1989)) in conical passage (412), attaching fitting (414), and using syringe (416) to drive the microparticles through inlet (102) and into planar cavity (106). After loading, holders (400), (402), (404), and (406) are removed from flow chamber (100), which is then mounted on the apparatus as shown in FIG. 1B.

Figure 5:
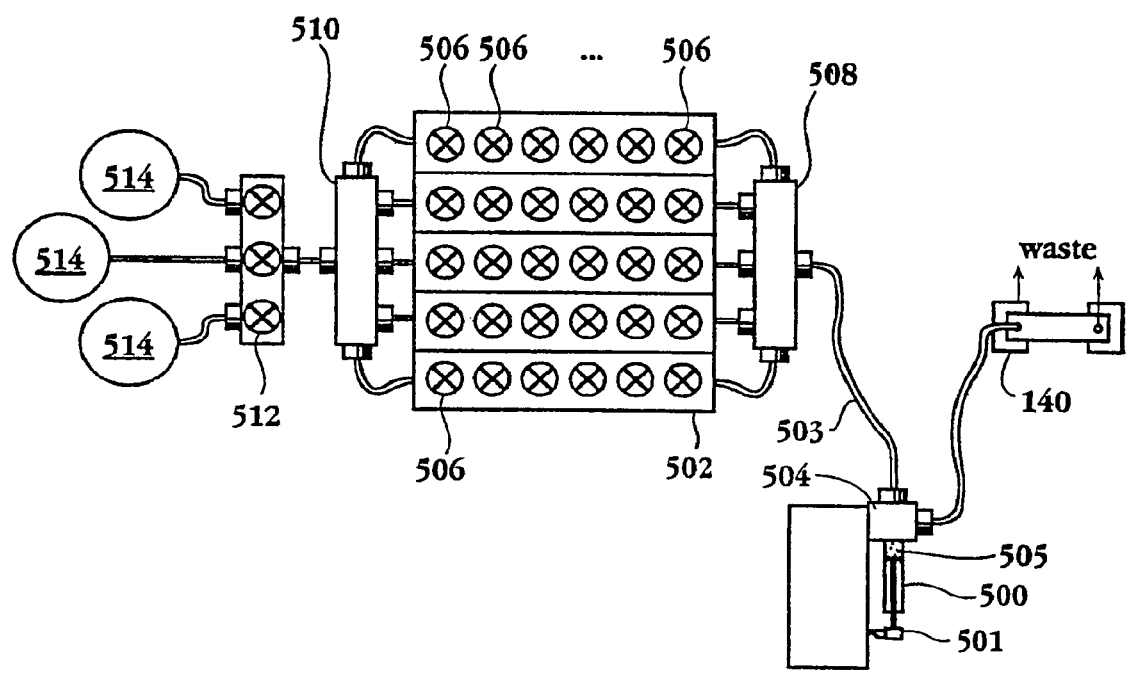
FIG. 5 is a schematic representation of a fluidics system for use with the invention.

Preferably, process reagents are delivered to flow chamber (100) by the fluidic system illustrated in FIG. 5 which has the capacity to handle many different reagents for complex analytical processes. In the illustrated embodiment, which is used in connection with DNA sequencing, the fluidics system may accommodate up to 38 reagents, including wash buffers, rinses, enzymes, hybridization probes, adaptors, and the like. Preferably, the function of the fluidics system is the sequential metering of selected processing reagents to flow chamber (100). Inlet (102) of flow chamber (100) is sealingly connected to holder (140) which contains rotary valve (actuator shown as 148) (not shown in FIG. 5). The function of the rotary valve is described above. A variety of means may be employed for moving processing reagents from reservoirs, through tubing, and into flow chamber (100), including gravity feed, pressure feed, and pumps, e.g. peristaltic, syringe, and the like. Preferably, common syringe pump (500) is employed for removing predetermined amounts processing reagents from reservoirs and for forcing such reagents through flow chamber (100) at a predetermined flow rate. Under control of computer (116), pump (500) in operational association with valve block (502) and rotary valve (504) removes a predetermined amount of processing reagent from a selected reservoir by siphoning reagent out of the reservoir on the out-stroke of plunger (501) of pump (500). On the instroke of plunger (501), rotary valve (504) directs processing reagent from tubing (503) to reservoir (505) of pump (500). On the out-stroke of plunger (501), state of rotary valve (504) is changed to direct processing reagent from reservoir (505) to inlet tubing (144). Tubing (503) connects rotary valve (504) with manifold (508) which, in turn, is connected to a plurality (five shown) of banks of zero dead volume valves (506). Zero dead volume valves (506) connect individual reservoirs holding processing reagents to a common passageway (not shown in FIG. 5) that runs through each of the banks of valves connecting to manifold (508).

A preferred zero dead volume valve is described in U.S. Pat. Nos. 4,558,845 and 4,703,913, which are incorporated by reference. Process reagents from reservoirs (514) are distributed to the banks of dead volume valves by way of manifold (510). Alternative valve blocks for controlling delivery of process reagents to flow chamber (100) include the valve matrix disclosed in U.S. Pat. No. 5,203,368.

Figure 6A:
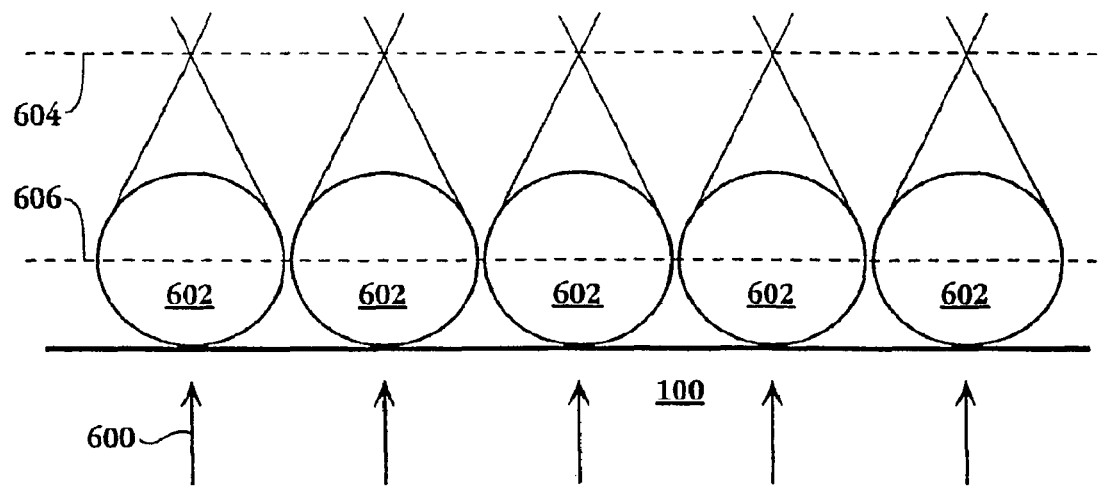
FIGS. 6A and 6B schematically illustrate top-lighting and back-lighting approaches for determining microparticle centers in an array.

An important feature of detection means (114) of the invention is the ability to keep track of individual microparticles through multiple process steps and/or cycles. In connection with such tracking, detection means (114) periodically records optical characteristics of individual microparticles that provide a close approximation microparticle centers. Preferably, when trans-illumination, or "back lighting" of flow chamber (100) is possible, the optical characteristic is the focused back light from the microparticles. That is, in reference to FIG. 6A, back light (600) passes vertically through flow chamber (100) where it is focused by microparticles (602) onto focal plane (604). The image of focal plane (604) in this configuration appears as a field of bright points, where each point is located at the approximate center of its corresponding microparticle. In an epiillumination system, light from above flow chamber (100), i.e. "top light (610)," is directed from a vertical direction onto microparticles (602) where it scatters from the top surface of the microparticles. In this configuration, the optical characteristic is the scatter center of a microparticle. Thus, an image is collected from the plane containing scatter centers (612) resulting from such top lighting. As with focused back lighting, the image of the scatter centers provides a convenient way to readily determine the approximate centers of the microparticles.

In the preferred image processing approach, once microparticle centers (700) are determined, pixels (702) are assigned for determining characteristics, e.g. intensity, of an optical signal generated at each microparticle (602). The size of micro particle (602) and pixel area determine how many pixels are assigned to each microparticle. In making such an assignment, important factors include the degree to which the calculated center of a microparticle (as described above) is likely to deviate from the geometric center, the extent to which optical signal collected from the edge of an image contains spurious information (e.g. signal from an overlapping or adjacent microparticle), the uniformity of microparticle diameter and shape, and the like. In the preferred apparatus of the invention, 5 μm diameter microparticles are employed and the pixel dimensions of the CCD detector are about 0.9 μm×0.9 μm. Thus, nine pixels fit easily within the interior of a microparticle image with a margin of at least about 1 μm between any pixel and the edge of the microparticle image. In the preferred embodiment, an initial pixel is assigned which encloses the computed center of a microparticle, e.g. pixel "5" in FIG. 7. Thereafter, additional pixels are assigned, usually the immediately adjacent pixels. Preferably, the value of the optical signal generated by a process at the surface of a microparticle is the average value of the optical signals collected by pixels assigned to that microparticle.

Figure 8:
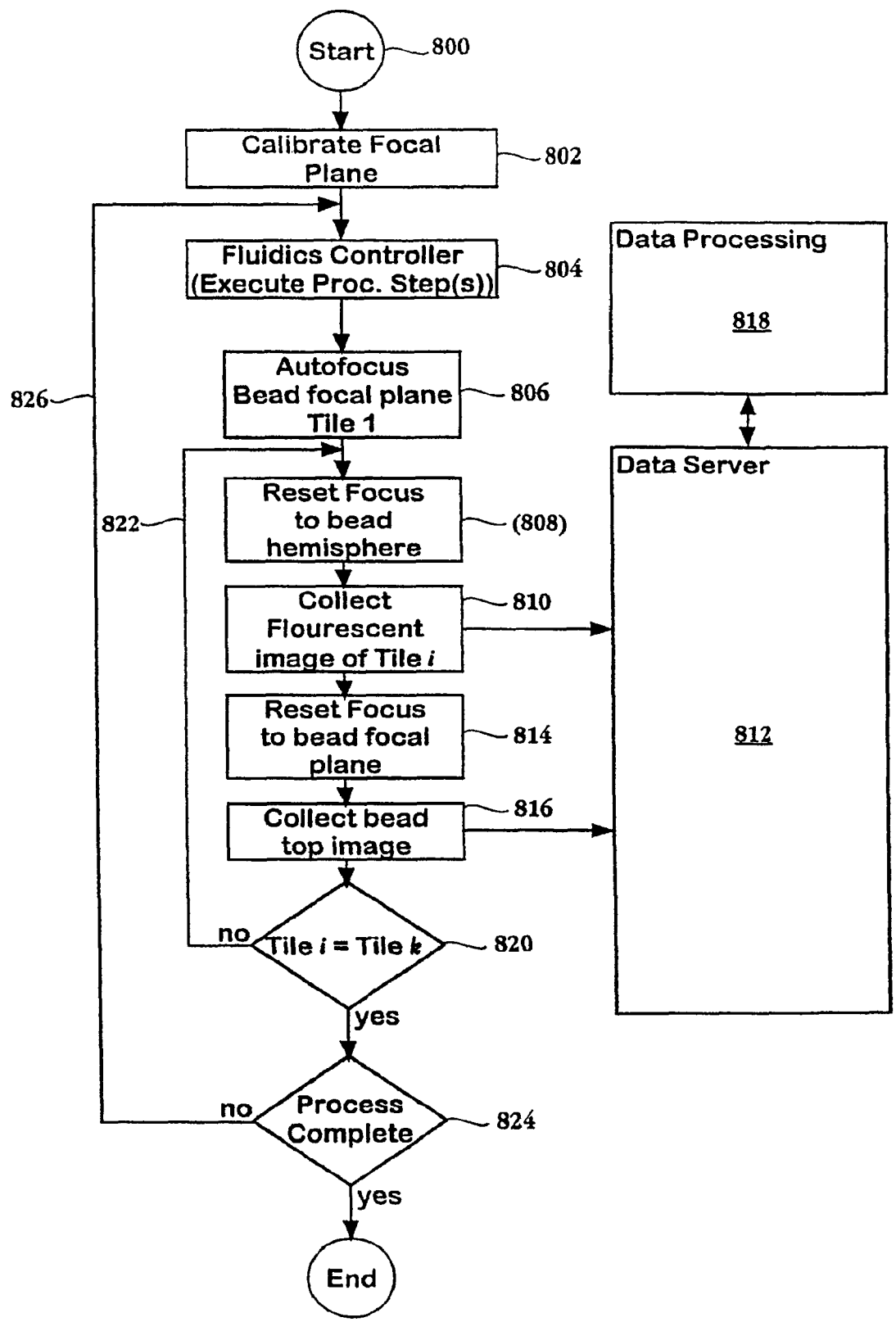
FIG. 8 is a flow chart summarizing operation of the system of the invention.

The general operation of the system of the preferred embodiment is summarized by the flow chart of FIG. 8. At the start (800) of an analysis, microparticles with anchored analytes have been loaded into flow chamber (100) which has been operationally mounted in holders 140 and 142. The initial operation is the calibration of the microparticle focal plane (802). That is, the vertical, or "z", position of the xyz-stage is determined which optimizes the focus of either the scatter centers of the microparticles, i.e. the microparticle tops for top-lighting, or the focus points of the microparticles for back-lighting. The optimization is carried out by a conventional autofocusing algorithm which provides an image contrast function constructed from a predetermined sample of regions within a collected image. For example, the contrast function may be evaluated iteratively for sequence of z-positions so that the differences of successive values of the contrast function can be determined. These are tested until a difference is found below a predetermined threshold, which is taken as the maximum of the contrast function. Focal plane location is taken as the z position which maximizes the image contrast function. Such calibration is carried out for each tile, if more than one tile is employed, so that a correction table is constructed of changes in stage setting values with respect to the settings of the first tile that are required to bring the system into focus upon translation to subsequent tiles. These values are stored by computer (116).

Figure 6B:
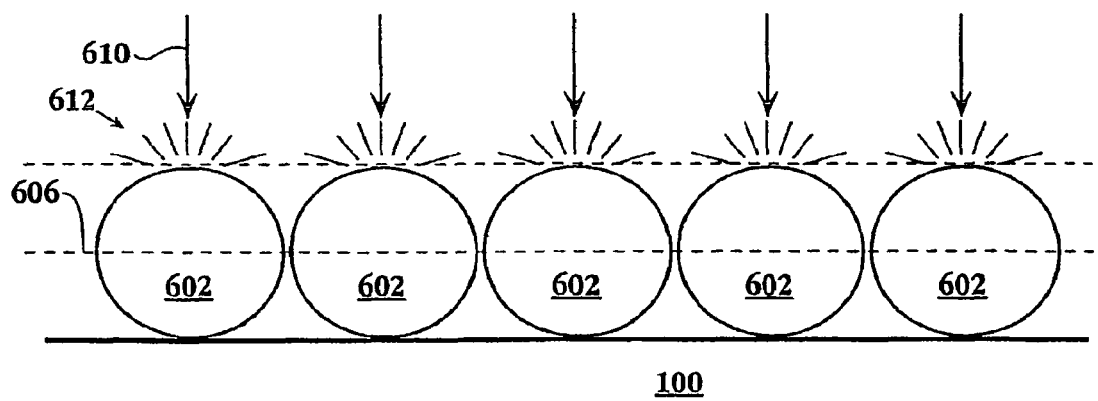

After calibration, process steps are initiated (804) by way of a fluidics controller operationally associated with computer (116). After process steps (804) are completed, stage settings are adjusted to place the first tile into focus using the autofocus algorithm (806), which places the focal plane of the microscope objective approximately at the tops of the microparticles. Stage settings are then adjusted (808) to bring the focal plane of the microscope objective to the approximate centers of the microparticles, as illustrated (606) in FIGS. 6A and 6B. The amount of stage movement in this re-focusing depends on the diameter of the microparticles being used. After appropriate selection of filters (124) and (122), a fluorescent image of the first tile is collected (810) and transferred to data server (812). Fluorescent images are collected on the plane of the microparticle centers because of imperfections in the planar array. That is, microparticles in planar cavity (106) do not lie in a perfect planar array for a variety of reasons. For example, some microparticles are elevated above others as a result of packing into the flow chamber; there is some variability in the size and shape of the microparticles; and, the floor of planar cavity (106) may be uneven. After the fluorescent image is collected, the focal plane of the microscope objective is returned (814) to the microparticle focal plane, where another image is collected (816) for the purpose of computing microparticle centers as described above. The image of micro particle centers is transferred to data server (812) where data processor (818) assigns pixels of the fluorescent image to each microparticle center, as described above. After the image of micro particle centers is collected (816), the stage is moved so that an image of the next tile can be collected (822). If there are no further tiles of microparticles (820), then the next steps and/or cycles of the process are executed (826). If there are no further process steps (824), then the process is complete and the apparatus is placed in a holding mode.

Optical signals collected in the course of analysis may be generated by a variety of mechanisms, including absorption and fluorescence, chemiluminescence, electrochemiluminescence, or bioluminescence emission. Extensive guidance is available for selecting appropriate optical signaling means, e.g. Kessler, editor, Nonradioactive Labeling and Detection of Biomolecules (Springer-Verlag, Berlin); Keller and Manak, DNA Probes, Second Edition (Stockton Press, New York, 1993); and the like. Preferably, optical signals generated in processing steps are fluorescence emissions.

Microparticles

An important feature of the system of the invention is the use of micro particles for carrying analytes. A variety of microparticles may be employed depending on particular applications. Generally, microparticles must consist of a material compatible with the reagents and chemistry of the process steps being carried out and microparticle must be substantially mechanically rigid so that they retain their shape and size during process steps. Preferably, as used herein, the term "substantially mechanically rigid" means that microparticles neither swell nor contract by more than ten percent (as measure by diameter) in any process solvent or reagent. Preferably, microparticles are micro spheres of uniform size, i.e. microparticles are monodisperse. More preferably, the diameters of spherical microparticles have a coefficient of variation less than five percent, and most preferably, less than two percent. Microparticle diameters are in the range of from 0.1 μm to 100 μm. Preferably, microparticle diameters range from 1 μm to 20 μm. Most preferably, microparticle diameters are in the range of 1 to 5 μm. Suitable microparticle materials include inorganic support materials such as glass, e.g. controlled-pore glass, Balltoni beads; silica, zirconia, and the like, e.g. Weetall, Methods in Enzymology, 44:134-148 (1976); and organic support materials such as highly crosslinked polystyrene, polyacrylate, polymethylmethacrylate, glycidylmethacrylate (GMA), Dynabeads (Dynal, Oslo, Norway), and the like, Rembaum et al., U.S. Pat. No. 4,046,720; Hodge and Sherrington, editors, pages 435-456, Polymer-supported Reactions in Organic Synthesis (Wiley & Sons, New York, 1980); Andrus et al., U.S. Pat. No. 5,047,524; and the like.

Attaching Identical Copies of Polynucleotides to Microparticles by Solid Phase Cloning In a preferred embodiment of the invention, identical copies of polynucleotides from a population are anchored to separate microparticles by solid phase cloning, i.e. the use of oligonucleotide tags for sorting polynucleotides onto microparticles such that only the same kind of polynucleotide will be attached to the same microparticle, e.g. Brenner, U.S. Pat. No. 5,604,097, which is incorporated by reference. This condition is accomplished by taking a sample of the full ensemble of tag-polynucleotide conjugates. (It is acceptable that identical polynucleotides have different tags, as it merely results in the same polynucleotide being operated on or analyzed twice in two different locations.) Such sampling can be carried out either overtly—for example, by taking a small volume from a larger mixture—after the tags have been attached to the polynucleotides, it can be carried out inherently as a secondary effect of the techniques used to process the polynucleotides and tags, or sampling can be carried out both overtly and as an inherent part of processing steps.

Oligonucleotide tags for use with the invention are members of a minimally cross-hybridizing set of oligonucleotides. The sequences of oligonucleotides of such a set differ from the sequences of every other member of the same set by at least two nucleotides: Thus, each member of such a set cannot form a duplex (or triplex) with the complement of any other member with less than two mismatches. Complements of oligonucleotide tags of the invention, referred to herein as "tag complements," may comprise natural nucleotides or non-natural nucleotide analogs. Tag complements are attached to microparticles.

Minimally cross-hybridizing sets of oligonucleotide tags and tag complements may be synthesized either combinatorially or individually depending on the size of the set desired and the degree to which cross-hybridization is sought to be minimized (or stated another way, the degree to which specificity is sought to be enhanced). For example, a minimally cross-hybridizing set may consist of a set of individually synthesized 10-mer sequences that differ from each other by at least 4 nucleotides, such set having a maximum size of 332 (when composed of 3 kinds of nucleotides and counted using a computer program such as disclosed in Appendix Ic of International patent application PCT/US96/09513). Alternatively, a minimally cross-hybridizing set of oligonucleotide tags may also be assembled combinatorially from subunits which themselves are selected from a minimally cross-hybridizing set. For example, a set of minimally cross-hybridizing 12-mers differing from one another by at least three nucleotides may be synthesized by assembling 3 subunits selected from a set of minimally cross-hybridizing 4-mers that each differ from one another by three 3 nucleotides. Such an embodiment gives a maximally sized set of $9^3$, or 729, 12-mers, "9" is number of oligonucleotides generated by the computer program of Appendix Ia of International patent application PCT/US96/09513, which assumes, as with the 10-mers, that only 3 of the 4 different types of nucleotides are used. The set is described as "maximal" because the computer programs disclosed in International patent application PCT/US96/09513 provide the largest set for a given input (e.g. length, composition, difference in number of nucleotides between members). Additional minimally crosshybridizing sets may be formed from subsets of such calculated sets.

When synthesized combinatorially, an oligonucleotide tag of the invention preferably consists of a plurality of subunits, each subunit consisting of an oligonucleotide of 3 to 9 nucleotides in length wherein each subunit is selected from the same minimally cross-hybridizing set. In such embodiments, the number of oligonucleotide tags available depends on the number of subunits per tag and on the length of the subunits.

As used herein in reference to oligonucleotide tags and tag complements, the term "repertoire" means the set of minimally cross-hybridizing set of oligonucleotides that make up the tags in a particular embodiment or the corresponding set of tag complements.

Preferably, in constructing a cDNA library where substantially all different cDNAs have different tags, a tag repertoire is employed whose complexity, or number of distinct tags, greatly exceeds the total number of mRNAs extracted from a cell or tissue sample. Preferably, the complexity of the tag repertoire is at least 10 times that of the polynucleotide population; and more preferably, the complexity of the tag repertoire is at least 100 times that of the polynucleotide population. Below, a protocol is disclosed for cDNA library construction using a primer mixture that contains a full repertoire of exemplary 9-word tags. Such a mixture of tag-containing primers has a complexity of $8^9$, or about $1.34 \times 10^8$. As indicated by Winslow et al., Nucleic Acids Research, 19:3251-3253 (1991), mRNA for library construction can be extracted from as few as $5 \times 10^5$ mammalian cells. Since a single mammalian cell contains about $5 \times 10^5$ copies of mRNA molecules of about $3.4 \times 10^4$ different kinds, by standard techniques one can isolate the mRNA from about 100 cells, or (theoretically) about $5 \times 10^7$ mRNA molecules. Comparing this number to the complexity of the primer mixture shows that without any additional steps, and even assuming that mRNAs are converted into cDNAs with perfect efficiency (1% efficiency or less is more accurate), the cDNA library construction protocol results in a population containing no more than 37% of the total number of different tags. That is, without any overt sampling step at all, the protocol inherently generates a sample that comprises 37%, or less, of the tag repertoire. The probability of obtaining a double under these conditions is about 5%, which is within the preferred range. With mRNA from 10 cells, the fraction of the tag repertoire sampled is reduced to only 3.7%, even assuming that all the processing steps take place at 100% efficiency. In fact, the efficiencies of the processing steps for constructing cDNA libraries are very low, a "rule of thumb" being that good library should contain about $10^8$ cDNA clones from mRNA extracted from $10^6$ mammalian cells.

Use of larger amounts of mRNA in the above protocol, or for larger amounts of polynucleotides in general, where the number of such molecules exceeds the complexity of the tag repertoire, a tag-polynucleotide conjugate mixture potentially contains every possible pairing of tags and types of mRNA or polynucleotide. In such cases, overt sampling may be implemented by removing a sample volume after a serial dilution of the starting mixture of tag-polynucleotide conjugates. The amount of dilution required depends on the amount of starting material and the efficiencies of the processing steps, which are readily estimated.

If mRNA were extracted from $10^6$ cells (which would correspond to about 0.5 µg of poly(A)$^+$ RNA), and if primers were present in about 10-100 fold concentration excess—as is called for in a typical protocol, e.g. Sambrook et al, Molecular Cloning, Second Edition, page 8.61 [10 µL 1.8 kb mRNA at 1 mg/mL equals about $1.68 \times 10^{-11}$ moles and 10 µL 18-mer primer at 1 mg/mL equals about $1.68 \times 10^{-9}$ moles], then the total number of tag-polynucleotide conjugates in a cDNA library would simply be equal to or less than the starting number of mRNAs, or about $5 \times 10^{11}$ vectors containing tag-polynucleotide conjugates—again this assumes that each step in cDNA construction—first strand synthesis, second strand synthesis, ligation into a vector—occurs with perfect efficiency, which is a very conservative estimate. The actual number is significantly less.

If a sample of n tag-polynucleotide conjugates are randomly drawn from a reaction mixture—as could be effected by taking a sample volume, the probability of drawing conjugates having the same tag is described by the Poisson distribution, $P(r) = e^{-\lambda}(\lambda)^r/r$, where r is the number of conjugates having the same tag and $\lambda = np$, where p is the probability of a given tag being selected. If $n = 10^6$ and $p = 1/(1.34 \times 10^8)$, then $\lambda = 0.00746$ and $P(2) = 2.76 \times 10^{-5}$. Thus, a sample of one million molecules gives rise to an expected number of doubles well within the preferred range. Such a sample is readily obtained as follows: Assume that the $5 \times 10^{11}$ mRNAs are perfectly converted into $5 \times 10^{11}$ vectors with tag-cDNA conjugates as inserts and that the $5 \times 10^{11}$ vectors are in a reaction solution having a volume of 100 µl. Four 10-fold serial dilutions may be carried out by transferring 10 µl from the original solution into a vessel containing 90 µl of an appropriate buffer, such as TE. This process may be repeated for three additional 5 dilutions to obtain a 100 µl solution containing $5 \times 10^5$ vector molecules per µl. A 2 µl aliquot from this solution yields $10^6$ vectors containing tag-cDNA conjugates as inserts. This sample is then amplified by straight forward transformation of a competent host cell followed by culturing.

Of course, as mentioned above, no step in the above process proceeds with perfect efficiency. In particular, when vectors are employed to amplify a sample of tag-polynucleotide conjugates, the step of transforming a host is very inefficient. Usually, no more than 1% of the vectors are taken up by the host and replicated. Thus, for such a method of amplification, even fewer dilutions would be required to obtain a sample of $10^6$ conjugates.

A repertoire of oligonucleotide tags can be conjugated to a population of polynucleotides in a number of ways, including direct enzymatic ligation, amplification, e.g. via PCR, using primers containing the tag sequences, and the like. The initial ligating step produces a very large population of tag-polynucleotide conjugates such that a single tag is generally attached to many different polynucleotides. However, as noted above, by taking a sufficiently small sample of the conjugates, the probability of obtaining "doubles," i.e. the same tag on two different polynucleotides, can be made negligible. Generally, the larger the sample the greater the probability of obtaining a double. Thus, a design trade-off exists between selecting a large sample of tag-polynucleotide conjugates—which, for example, ensures adequate coverage of a target polynucleotide in a shotgun sequencing operation or adequate representation of a rapidly changing mRNA pool, and selecting a small sample which ensures that a minimal number of doubles will be present. In most embodiments, the presence of doubles merely adds an additional source of noise or, in the case of sequencing, a minor complication in scanning and signal processing, as microparticles giving multiple fluorescent signals can simply be ignored.

As used herein, the term "substantially all" in reference to attaching tags to molecules, especially polynucleotides, is meant to reflect the statistical nature of the sampling procedure employed to obtain a population of tag-molecule conjugates essentially free of doubles. The meaning of substantially all in terms of actual percentages of tag-molecule conjugates depends on how the tags are being employed. Preferably, for nucleic acid sequencing, substantially all means that at least eighty percent of the polynucleotides have unique tags attached. More preferably, it means that at least ninety percent of the polynucleotides have unique tags attached. Still more preferably, it means that at least ninety-five percent of the polynucleotides have unique tags attached. And, most preferably, it means that at least ninety-nine percent of the polynucleotides have unique tags attached.

Tags can be conjugated to cDNAs of existing libraries by standard cloning methods. cDNAs are excised from their existing vector, isolated, and then ligated into a vector containing a repertoire of tags. Preferably, the tag-containing vector is linearized by cleaving with two restriction enzymes so that the excised cDNAs can be ligated in a predetermined orientation. The concentration of the linearized tag-containing vector is in substantial excess over that of the cDNA inserts so that ligation provides an inherent sampling of tags.

A general method for exposing the single stranded tag after amplification involves digesting a target polynucleotide-containing conjugate with the 5'→3' exonuclease activity of T4 DNA polymerase, or a like enzyme, e.g. as described in Kuijper et at., Gene, 112:147-155 (1992). When used in the presence of a single deoxynucleoside triphosphate, such a polymerase will cleave nucleotides from 3' recessed ends present on the non-template strand of a double stranded fragment until a complement of the single deoxynucleoside triphosphate is reached on the template strand. When such a nucleotide is reached the 5'→3' digestion effectively ceases, as the polymerase's extension activity adds nucleotides at a higher rate than the excision activity removes nucleotides. Consequently, single stranded tags constructed with three nucleotides are readily prepared for loading onto solid phase supports.

After the oligonucleotide tags are prepared for specific hybridization, e.g. by rendering them single stranded as described above, the polynucleotides are mixed with microparticles containing the complementary sequences of the tags under conditions that favor the formation of perfectly matched duplexes between the tags and their complements. There is extensive guidance in the literature for creating these conditions. Exemplary references providing such guidance include Wetmur, Critical Reviews in Biochemistry and Molecular Biology, 26:227-259 (1991); Sambrook et al., Molecular Cloning: A Laboratory Manual, 2nd Edition (Cold Spring Harbor Laboratory, New York, 1989); and the like. Preferably, the hybridization conditions are sufficiently stringent so that only perfectly matched sequences form stable duplexes. Under such conditions the polynucleotides specifically hybridized through their tags may be ligated to the complementary sequences attached to the microparticles. Finally, the microparticles are washed to remove polynucleotides with unligated and/or mismatched tags.

Preferably, for sequencing applications, standard CPG beads of diameter in the range of 20-50)µm are loaded with about $10^5$ polynucleotides, and glycidalmethacrylate (GMA) beads available from Bangs Laboratories (Carmel, Ind.) of diameter in the range of 5-10 µm are loaded with a few tens of thousand polynucleotide, e.g. $4 \times 10^4$ to $6 \times 10^4$, to a hundred thousand polynucleotides.

DNA Sequencing

Polynucleotides loaded onto microparticles may be simultaneously sequenced in the instant apparatus using a "base-by-base" DNA sequencing methodology. Such sequencing methodology permits the stepwise identification of a sequence of nucleotides in a target polynucleotide, usually one base at a time, through successive cycles of treatment and detection. Base-by-base approaches are disclosed in the following references: Cheeseman, U.S. Pat. No. 5,302,509; Tsien et al., International application WO 91/06678; Rosenthal et al., International application WO 93/21340; Canard et al., Gene, 148:1-6 (1994); Metzker et al, Nucleic Acids Research, 22:4259-4267 (1994); and the like. Preferably, the base-by-base approach disclosed by Brenner in U.S. Pat. No. 5,599,675 is used with the apparatus of the invention to sequence polynucleotides on a population of loaded microparticles disposed as a planar array in the flow chamber. Accordingly, Brenner, U.S. Pat. No. 5,599,675 is incorporated by reference. Preferably, the a population of loaded microparticles for sequencing includes at least ten thousand loaded microparticles; more preferably, such a population includes at least fifty thousand loaded microparticles; and still more preferably, such a population includes at least one hundred thousand loaded microparticles.

Preferably, the sequencing method of Brenner (cited above) is employed in the embodiment disclosed in Albrecht et al. International patent application PCT/US97/09472 which discloses the use of encoded adaptors. An encoded adaptor is a double stranded oligonucleotide comprising a protruding strand and an oligonucleotide tag selected from a minimally cross-hybridizing set of oligonucleotides. Encoded adaptors whose protruding strands form perfectly matched duplexes with the complementary protruding strands of the target polynucleotide are ligated. After ligation, the identity and ordering of the nucleotides in the protruding strands are determined, or "decoded," by specifically hybridizing a labeled tag complement to its corresponding tag on the ligated adaptor. Encoded adaptors may be used in an adaptor-based method of DNA sequencing that includes repeated cycles of ligation, identification, and cleavage, such as the method described in Brenner (cited above). Briefly, such a method comprises the following steps: (a) ligating an encoded adaptor to an end of a polynucleotide, the encoded adaptor having a nuclease recognition site of a nuclease whose cleavage site is separate from its recognition site; (b) identifying one or more nucleotides at the end of the polynucleotide by the identity of the encoded adaptor ligated thereto; (c) cleaving the polynucleotide with a nuclease recognizing the nuclease recognition site of the encoded adaptor such that the polynucleotide is shortened by one or more nucleotides; and (d) repeating said steps (a) through (c) until said nucleotide sequence of the polynucleotide is determined. In the identification step, successive sets of tag complements are specifically hybridized to the respective tags carried by encoded adaptors ligated to the ends of the target polynucleotides, as described above. The type and sequence of nucleotides in the protruding strands of the polynucleotides are identified by the label carried by the specifically hybridized tag complement and the set from which the tag complement came.

Construction and Sorting of cDNA Library for Signature Sequencing with Encoded Adaptors In this example, a cDNA library is constructed in which an oligonucleotide tag consisting of 8 four-nucleotide "words" is attached to each cDNA. As described above, the repertoire of oligonucleotide tags of this size is sufficiently large (about $10^8$) so that if the cDNAs are synthesized from a population of about $10^6$ mRNAs, then there is a high probability that each cDNA will have a unique tag for sorting. After mRNA extraction, first strand synthesis is carried out in the presence of 5-Me-dCTP (to block certain cDNA restriction sites) and a biotinylated primer mixture containing the oligonucleotide tags. After conventional second strand synthesis, the tag-cDNA conjugates are cleaved with Dpn II (which is unaffected by the 5-Me-deoxycytosines), the biotinylated portions are separated from the reaction mixture using streptavidin-coated magnetic beads, and the tag cDNA conjugates are recovered by cleaving them from the magnetic beads via a Bsm BI site carried by the biotinylated primer. The Bsm BI-Dpn II fragment containing the tag cDNA conjugate is then inserted into a plasmid and amplified. After isolation of the plasmids, tag-cDNA conjugates are amplified out of the plasmids by PCR in the presence of 5-Me-dCTP, using biotinylated and fluorescently labeled primers containing predefined restriction endonuclease sites. After affinity purification with streptavidin coated magnetic beads, the tag-cDNA conjugates are cleaved from the beads, treated with T4 DNA polymerase in the presence of dGTP to render the tags single stranded, and then combined with a repertoire of GMA beads having tag complements attached. After stringent hybridization and ligation, the GMA beads are sorted via FACS to produce an enriched population of GMA beads loaded with cDNAs. The enriched population of loaded GMA beads are immobilized in a planar array in a flow chamber where base-by-base sequence takes place using encoded adaptors, as disclosed in Albrecht et al., International patent application PCT/US97/09472.

Approximately 5 μg of poly($A^+$) mRNA is extracted from DBY746 yeast cells using conventional protocols. First and second strand cDNA synthesis is carried out by combining 100-150 pmoles of the following primer (SEQ ID NO: 1):

5'-biotin-ACTAAT<u>CGTCTC</u>ACTAT<u><u>TTAATTAA</u></u>[W, W, W, G]$_8$

CC(T)$_{18}$V-3' with the poly(A+) mRNA using a Stratagene (La Jolla, Calif.) cDNA Synthesis Kit in accordance with the manufacturer's protocol. This results in cDNAs whose first stand deoxycytosines are methylated at the 5-carbon position. In the above formula, "V" is G, C, or A, "[W,W,W,G]" is a four-nucleotide word selected from Table II of Brenner, International patent application PCT/US96/09513, the single underlined portion is a Bsm BI recognition site, and the double underlined portion is a Pac I recognition site. After size fractionation (GOBCO-BRL cDNA Size Fractionation Kit) using conventional protocols, the cDNAs are digested with Dpn II (New England Bioscience, Beverly, Mass.) using manufacturer's protocol and affinity purified with streptavidin-coated magnetic beads (M-280 beads, Dynal A.S., Oslo, Norway). The DNA captured by the beads is digested with Bsm BI to release the tag-cDNA conjugates for cloning into a modified pBCSK$^-$ vector (Stratagene, La Jolla, Calif.) using standard protocols. The pBCSK$^-$ vector is modified by adding a Bbs I site by inserting the following fragment (SEQ ID NO: 2) into the Kpn I/Eco RV digested vector.

CGAAGACCC

3'-CATGGCTTCTGGGGATA-5'

Bsm BI/Dpn II digested tag-cDNA conjugate is inserted in the pBCSK$^-$ which is previously digested with Bbs I and Bam HI. After ligation, the vector is transfected into the manufacturer's recommended host for amplification.

After isolating the above pBCSK$^-$ vector from a standard plasmid miniprep, the tag-cDNA conjugates are amplified by PCR in the presence of S-Me-dCTP using 20-mer primers complementary to vector sequences flanking the tag-cDNA insert. The "upstream" primer, i.e. adjacent to the tag, is biotinylated and the "downstream" primer, i.e. adjacent to the cDNA, is labeled with fluorescein. After amplification, the PCR product is affinity purified then cleaved with Pac I to release fluorescently labeled tagcDNA conjugates. The tags of the conjugates are rendered single stranded by treating them with T4 DNA polymerase in the presence of dGTP. After the reaction is quenched, the tag-cDNA conjugate is purified by phenol-chloroform extraction and combined with 5.5 mm GMA beads carrying tag complements, each tag complement having a 5' phosphate. Hybridization is conducted under stringent conditions in the presence of a thermal stable ligase so that only tags forming perfectly matched duplexes with their complements are ligated. The GMA beads are washed and the loaded beads are concentrated by FACS sorting, using the fluorescently labeled cDNAs to identify loaded GMA beads. The tag-cDNA conjugates attached to the GMA beads are digested with Dpn II to remove the fluorescent label and treated with alkaline phosphatase to prepare the cDNAs for sequencing. That is, phosphatase is used to remove the 5' phosphate from the ends of the cDNAs to prevent unwanted cDNA-cDNA ligations by way of the palindromic Dpn II site.

The following cleavage adaptor (SEQ ID NO: 3) is ligated to the Dpn II-digested and phosphatase treated cDNAs:

```
5'-pGATCAGCTGCTGCAAATTT
    pTCGACGACGTTTAAA
```

After ligation, the 3' phosphate is removed by alkaline phosphatase, the 5' strand of the cDNA is treated with T4 DNA kinase, and the nick between the cleavage adaptor and cDNA is ligated. After cleavage by Bbv I, encoded adaptors are ligated to the ends of the cDNAs and the beads are ready for loading into the flow chamber.

Ligation of the adaptors to the target polynucleotide is carried out in a mixture consisting of 5 µl beads (20 mg), 3 µL NEB 10× ligase buffer, 5 µL adaptor mix (25 nM), 2.5 µL NEB T4 DNA ligase (2000 units/µL), and 14.5 µL distilled water. The mixture is incubated at 16° C. for 30 minutes, after which the beads are washed 3 times in TE (pH 8.0).

After centrifugation and removal of TE, the 3' phosphates of the ligated adaptors are removed by treating the polynucleotide-bead mixture with calf intestinal alkaline phosphatase (CIP) (New England Biolabs, Beverly, Mass.), using the manufacturer's protocol. After removal of the 3' phosphates, the CIP may be inactivated by proteolytic digestion, e.g. using Pronase™ (available form Boeringer Mannhiem, Indianapolis, Ind.), or an equivalent protease, with the manufacturer's protocol. The polynucleotide-bead mixture is then washed, treated with a mixture of T4 polynucleotide kinase and T4 DNA ligase (New England Biolabs, Beverly, Mass.) to add a 5' phosphate at the gap between the target polynucleotide and the adaptor, and to complete the ligation of the adaptors to the target polynucleotide. The bead-polynucleotide mixture is then washed in TE, diluted to a concentration of approximately 100 thousand beads per µL, and 5 µL of the resulting solution is loaded into a flow chamber with the help of the holders of FIG. 4.

The top strands of the following 16 sets of 64 encoded adaptors (SEQ ID NO: 4 through SEQ ID NO: 19) are each separately synthesized on an automated DNA synthesizer (model 392 Applied Biosystems, Foster City) using standard methods. The bottom strand, which is the same for all adaptors, is synthesized separately then hybridized to the respective top strands:

| SEQ ID NO. | Encoded Adaptor |
|---|---|
| 4 | 5'-pANNNTACAGCTGCATCCCttggcgctgagg<br>pATGCACGCGTAGGG-5' |
| 5 | 5'-pNANNTACAGCTGCATCCCtgggcctgtaag<br>pATGCACGCGTAGGG-5' |
| 6 | 5'-pCNNNTACAGCTGCATCCCttgacgggtctc<br>pATGCACGCGTAGGG-5' |
| 7 | S'-pNCNNTACAGCTGCATCCCtgcccgcacagt<br>pATGCACGCGTAGGG-5' |
| 8 | 5'-pGNNNTACAGCTGCATCCCttcgcctcggac<br>pATGCACGCGTAGGG-5' |
| 9 | 5'-pNGNNTACAGCTGCATCCCtgatccgctagc<br>pATGCACGCGTAGGG-S' |
| 10 | 5'-pTNNNTACAGCTGCATCCCttccgaacccgc<br>pATGCACGCGTAGGG-5' |
| 11 | 5'-pNTNNTACAGCTGCATCCCtgaggggatag<br>pATGCACGCGTAGGG-5' |
| 12 | 5'-pNNANTACAGCTGCATCCCttcccgctacac<br>pATGCACGCGTAGGG-S' |
| 13 | 5'-pNNNATACAGCTGCATCCCtgactccccgag<br>pATGCACGCGTAGGG-5' |
| 14 | 5'-pNNCNTACAGCTGCATCCCtgtgttgcgcgg<br>pATGCACGCGTAGGG-5' |
| 15 | 5'-pNNNCTACAGCTGCATCCCtctacagcagcg<br>pATGCACGCGTAGGG-5' |
| 16 | 5'-pNNGNTACAGCTGCATCCCtgtcgcgtcgtt<br>pATGCACGCGTAGGG-5' |
| 17 | 5'-pNNNGTACAGCTGCATCCCtcggagcaacct<br>pATGCACGCGTAGGG-5' |
| 18 | 5'-pNNTNTACAGCTGCATCCCtggtgaccgtag<br>pATGCACGCGTAGGG-5' |
| 19 | 5'-pNNNTTACAGCTGCATCCCtcccctgtcgga<br>pATGCACGCGTAGGG-5' | where N and p are as defined above, and the nucleotides indicated in lower case letters are the 12-mer oligonucleotide tags. Each tag differs from every other by 6 nucleotides. Equal molar quantities of each adaptor are combined in NEB #2 restriction buffer (New England Biolabs, Beverly, Mass.) to form a mixture at a concentration of 1000 pmol/µL.

Each of the 16 tag complements are separately synthesized as amino-derivatized oligonucleotides and are each labeled with a fluorescein molecule (using an NHS-ester of fluorescein, available from Molecular Probes, Eugene, Oreg.) which is attached to the 5' end of the tag complement through a polyethylene glycol linker (Clonetech Laboratories, Palo Alto, Calif.). The sequences of the tag complements are simply the 12-mer complements of the tags listed above.

A flow chamber of the design shown in FIGS. 2A and 2B is employed in association with an Olympus Optical Co., Ltd. (Tokyo, Japan) model BX60MF5 fluorescent microscope fitted with a model U-ULS75XE 75 watt Xenon arc lamp, a motorized filter wheel, a Ludl Electronic Products, Ltd. computer-controlled stage, and a Photometries, Ltd. (Tucson, Ariz.) PXL CCD camera with a 2000×2000 pixel array. Appropriate bandpass filters (122) and (124) are employed for exciting fluorescein and transmitting fluorescent signal to CCD camera (120). Microparticle positions are determined by top-lighting with broadband light from Xenon lamp (126) reduced by a factor of about $10^{-4}$ with a neutral density filter. Fluorescent images are collected with about 2 minute exposure times.

Figure 7:
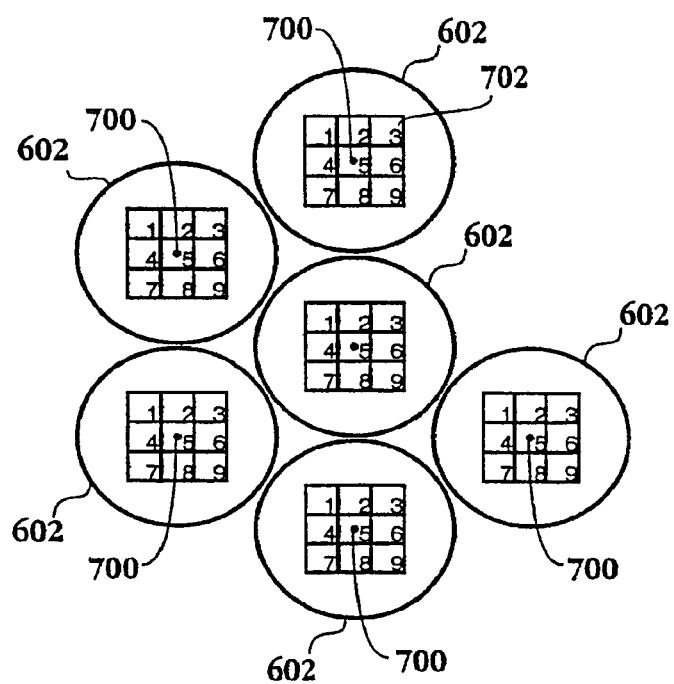
FIG. 7 schematically illustrates the assignment of pixels to microparticles for data processing.

Height (204) of flow chamber (201) is selected to be 7 μm, or approximately 140% of the diameter of the GMA beads. Width (210) of flow chamber (201) is selected so as to ensure that a 3×3 array of 9 image pixels will cover approximately 40-60% of a bead's image after 10× magnification (as illustrated in FIG. 7). Thus, in order to capture images of tiles of about 100 thousand 5 μm GMA beads, width (210) is selected to have a value of 1.7 mm. Length (212) is selected so that the flow chamber can hold from 1 to 10 tiles of about one hundred thousand 5 μm diameter beads each. The cross section (220) of inlet passage (214) matches that of the inlet tubing and gradually enlarges to match that of flow chamber (201) in the region of the planar cavity, i.e. the region holding the GMA beads on which analysis is performed. It is desirable to have a constant cross section through the planar cavity of flow chamber (201) to minimize the creation of non-uniform flow patterns, as might occur with sudden constrictions and/or expansions in cross section. Both body (218) and cover (216) of flow chamber (201) are glass, and the planar cavity and channels of body (218) are formed by standard chemical etching techniques. Cross section (222) of outlet passage (224) is selected to match the cross section of flow chamber (201) at dam (202).

The fluidics system of FIG. 5a which includes all valves, syringe pump (500), and Peltier block (152), is controlled by code written in LabVIEW 5.0 (National Instruments, Austin, Tex.) and run on a Compact Deskpro Pentium-based microprocessor, which is connected to the various components of the fluidics system by standard 110 circuit boards. Detection system (114) and overall control of the instrument is effected through a Sun Microsystems (Mountain View, Calif.) Sparcstation 5.

Three cycles of ligation, identification, and cleavage are carried out in flow chamber (201) to give the sequences of 12 nucleotides at the termini of each of approximately 500,000 cDNAs. That is, five tiles of GMA beads are analyzed in the following series of process steps:
1. Calibrate focal plane of GMA beads.
2. Hybridize decoder.
3. Autofocus on tile 1.
4. Set focus to bead centers.
5. Collect fluorescent image.
6. Set focus to bead focal plane (scatter centers).
7. Collect image.
8. Repeat steps 4-7 for remaining tiles.
9. Wash.
10. Repeat steps 2-9 for remaining decoders.
11. Cleave encoded adaptor.
12. Wash.
13. Ligate top strand of next encoded adaptor.
14. Wash.
15. Repeat steps 13-14.
16. Kinase bottom strand of encoded adaptor.
17. Wash.
18. Ligate bottom strand of encoded adaptor.
19. Wash.
20. Repeat steps 2-9.
21. Repeat steps 11-19 for next encoded adaptor.

In steps 2-9, nucleotides of the cDNAs are identified by hybridizing tag complements to the encoded adaptors. Specifically hybridized tag complements are detected by exciting their fluorescent labels with illumination beam (110) from Xenon arc lamp (126). In step 13, encoded adaptors and T4 DNA ligase (Promega, Madison, Wn at about 0.75 units per μL are passed through the flow chamber at a flow rate of about 1-2 μL per minute for about 20-30 minutes at 16° C., after which wash of step 14 is executed by flowing, in succession, a solution of Pronase™ (Boehringer Mannheim, Indianapolis, Ind.), a salt wash solution, and an ethanol wash solution through the flow chamber, all with the same flow rate of 1-2 μL per minute and for durations of 15, 10, and 10 minutes, respectively. The salt wash solution is 150 mM NaCl and 10 mM Tris-HCl (pH 8.5), and the ethanol wash solution is 3:1 (v/v) solution of the salt wash solution and ethanol. The ligation and wash steps 13 and 14 are repeated once, after which the adaptors and the cDNAs are prepared for second strand ligation by passing T4 DNA kinase (New England Bioscience, Beverly, Mass.) at 7 units per μL through the flow chamber at 37° C. with a flow rate of 1-2 μL per minute for 15-20 minutes. Ligation of the second strand is carried out by flowing T4 DNA ligase (0.75 units per mL, Promega) through the flow chamber for 20-30 minutes at a rate of 1-2 μL per minute, followed by Pronase™ treatment and washing as described above. Tag complements at 25 nM concentration are passed through the flow chamber at a flow rate of 1-2 μL per minute for 10 minutes at 20° C., after which the fluorescent labels carried by the tag complements are illuminated and fluorescence is collected. The tag complements are melted from the encoded adaptors by passing NEB #2 restriction buffer with 3 mM $MgCl_2$ through the flow chamber at a flow rate of 1-2 μL per minute at 55° C. for 10 minutes. Encoded adaptors are cleaved from the cDNAs by passing Bbv I (New England Biosciences, Beverly, Mass.) at 1 unit μL at a flow rate of 1-2 μL per minute for 20 minutes at 37° C., followed by Pronase™ treatment and washing, as described above.

What is claimed is:

1. A method of sequencing multiple target polynucleotides in parallel using a sequencing system, comprising:

providing a flow chamber comprising a plurality of ridges within the flow chamber, the flow chamber comprising multiple microparticles immobilized between the ridges, each microparticle of the multiple microparticles including a target polynucleotide to be sequenced immobilized on the microparticle, the average distance between centers of adjacent microparticles being less than two microparticle diameters, and the ridges being of a height less than a diameter of a microparticle and of a length greater than a plurality of said diameters;

performing a sequence determination of the target polynucleotides immobilized on the microparticles in the flow cell; and obtaining data that provides information about the plurality of target polynucleotides based on the sequence determination.

2. The method of claim 1, wherein the plurality of ridges within the flow chamber run parallel to the axis of the flow chamber.

3. The method of claim 1, wherein the sequence determination comprises successive cycles of a base-by-base sequencing methodology.

4. The method of claim 1, wherein said obtaining data comprises using a data processor configured to receive data from the sequence determination to provide sequence data for the polynucleotides immobilized on the multiple microparticles.

5. The method of claim 4, wherein the data processor is further configured to track each microparticle through multiple rounds of label identification.

6. The method of claim 4, wherein the data processor is configured to receive data corresponding to the polynucleotides as they are processed in parallel.

7. The method of claim 1, wherein the number of microparticles per unit area in the planar array is at least eighty percent of the number of microparticles in a hexagonal array of equal area.

8. The method of claim 1, wherein the ridges are spaced such that the microparticles are arranged single-file between the ridges.

9. The method of claim 1, wherein multiple ridges in the flow chamber are parallel to each other.

10. The method of claim 1, wherein a distance between ridges is configured to allow for maximal packing of microparticles.

11. The method of claim 1, wherein a diameter of each of the multiple microparticles is approximately a same diameter.

12. The method of claim 1, wherein the multiple microparticles are chemically constrained in the flow chamber.

13. The method of claim 12, wherein the multiple microparticles are constrained by a crosslinked chemical attachment.

14. The method of claim 1, wherein said obtaining data comprises using a light source configured to provide an excitation beam and an optics system configured to receive light produced in response to the excitation beam.

15. The method of claim 1, wherein the sequencing system comprises a body attached to a plate to form the flow chamber.

16. The method of claim 1, wherein the multiple microparticles are connected to the flow chamber in a monolayer between the ridges, said monolayer comprising multiple tiles and a detector is configured to separately generate data based on a first subset of the multiple microparticles and a second subset of the multiple microparticles physically separate from the first subset of the multiple microparticles.

17. The method of claim 1, wherein at least 500,000 microparticles are immobilized in the flow chamber, each of the 500,000 microparticles comprising an analyte to be sequenced immobilized on the microparticle.

18. The method of claim 1, wherein the distance between the elongated ridges having multiple microparticles immobilized therebetween is greater than the diameter of a microparticle.

19. The method of claim 1, wherein the microparticles comprise a hexagonal array.

* * * * *